United States Patent
Beira

(10) Patent No.: US 10,548,680 B2
(45) Date of Patent: Feb. 4, 2020

(54) ARTICULATED HANDLE FOR MECHANICAL TELEMANIPULATOR

(71) Applicant: DistalMotion SA, Lausanne (CH)

(72) Inventor: Ricardo Daniel Rita Beira, Lausanne (CH)

(73) Assignee: Distalmotion SA, Epalinges (CH)

( * ) Notice: Subject to any disclaimer, the term of this patent is extended or adjusted under 35 U.S.C. 154(b) by 226 days.

(21) Appl. No.: 15/536,568

(22) PCT Filed: Dec. 18, 2015

(86) PCT No.: PCT/IB2015/002533
§ 371 (c)(1),
(2) Date: Jun. 15, 2017

(87) PCT Pub. No.: WO2016/097873
PCT Pub. Date: Jun. 23, 2016

(65) Prior Publication Data
US 2017/0360522 A1 Dec. 21, 2017

Related U.S. Application Data

(60) Provisional application No. 62/094,078, filed on Dec. 19, 2014.

(51) Int. Cl.
*A61B 34/00* (2016.01)
*A61B 34/37* (2016.01)
*A61B 17/29* (2006.01)

(52) U.S. Cl.
CPC .............. *A61B 34/77* (2016.02); *A61B 34/37* (2016.02); *A61B 2017/291* (2013.01)

(58) Field of Classification Search
CPC .......... A61B 34/77; A61B 34/70; A61B 34/71
See application file for complete search history.

(56) References Cited

U.S. PATENT DOCUMENTS 2,764,301 A 9/1956 Goertz et al.
2,771,199 A 11/1956 Jelatis
(Continued)

FOREIGN PATENT DOCUMENTS

CN 101584594 A 11/2009
CN 101637402 A 2/2010
(Continued)

OTHER PUBLICATIONS

US 9,232,978 B2, 01/2016, Shellenberger et al. (withdrawn)
(Continued)

*Primary Examiner* — Andrew Yang
(74) *Attorney, Agent, or Firm* — Eversheds Sutherland (US) LLP; Christopher C. Bolten; Nicola A. Pisano

(57) ABSTRACT

Disclosed is a mechanical telemanipulator handle to control surgical instruments with articulated end-effectors, such as dissectors, scissors or graspers, enhancing a surgeon's performance during various surgical procedures. These surgical instruments may be inserted into surgical incisions in a body of a patient and the articulated end-effector is mounted on the distal extremity of the instrument shaft, comprising a plurality of links interconnected by a plurality of joints, whose movements are remotely controlled at the telemanipulator's proximal handle. This remote actuation is accomplished through mechanical transmission, optimally along flexible elements, which are able to kinematically connect the end-effector with the handle such that the movements applied on the handle are reproduced by the end-effector at a predetermined scaled ratio. The articulated handle further comprises one or more movement-amplification systems that amplify the movements generated at the handle so that the gripping force at the instrument's end-effector can be increased and the surgeon's ergonomy improved.

12 Claims, 32 Drawing Sheets

(56) References Cited

U.S. PATENT DOCUMENTS

| | | |
|---|---|---|
| 2,774,488 A | 12/1956 | Goertz |
| 2,846,084 A | 8/1958 | Goertz et al. |
| 3,065,863 A | 11/1962 | Saunders, Jr. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker et al. |
| 4,221,516 A | 9/1980 | Haaker et al. |
| 4,756,655 A | 7/1988 | Jameson |
| 5,147,357 A | 9/1992 | Rose et al. |
| 5,176,352 A | 1/1993 | Braun |
| 5,207,114 A | 5/1993 | Salisbury et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,784,542 A | 7/1998 | Ohm et al. |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 | 5/2002 | Wallace et al. |
| 6,435,794 B1 | 8/2002 | Springer |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,602,287 B2 | 12/2013 | Yates et al. |
| 8,603,077 B2 | 12/2013 | Cooper et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |

(56) References Cited

U.S. PATENT DOCUMENTS

| | | |
|---|---|---|
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,861 B2 | 8/2015 | Martin et al. |
| 9,149,339 B2 | 10/2015 | Unsworth |
| 9,204,939 B2 | 12/2015 | Frimer et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,795,282 B2 | 10/2017 | Sholev et al. |
| 9,795,454 B2 | 10/2017 | Seeber et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,052,157 B2 | 8/2018 | Frimer et al. |
| 10,064,691 B2 | 9/2018 | Beira et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0314181 A1 | 12/2008 | Schena |
| 2009/0036902 A1 | 2/2009 | DiMaio et al. |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0299141 A1 | 12/2009 | Downey et al. |
| 2010/0004508 A1 | 1/2010 | Naito et al. |
| 2010/0023025 A1 | 1/2010 | Zeiner et al. |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1* | 6/2013 | Stefanchik ......... A61B 17/2909 606/1 |
| 2013/0172713 A1 | 7/2013 | Kirschenman |
| 2013/0245643 A1 | 9/2013 | Woodard et al. |
| 2013/0245647 A1 | 9/2013 | Martin et al. |
| 2013/0282027 A1 | 10/2013 | Woodard et al. |
| 2013/0303408 A1 | 11/2013 | Indermuhle |
| 2013/0304083 A1 | 11/2013 | Kaercher et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0200561 A1 | 7/2014 | Ingmanson et al. |
| 2014/0207150 A1 | 7/2014 | Rosa et al. |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |

(56) References Cited

U.S. PATENT DOCUMENTS

| | | |
|---|---|---|
| 2015/0142018 A1 | 5/2015 | Sniffin et al. |
| 2015/0150575 A1 | 6/2015 | Hartoumbekis et al. |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0374766 A1 | 12/2016 | Schuh |
| 2017/0245954 A1 | 8/2017 | Beira |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0028269 A1 | 2/2018 | Morel et al. |
| 2018/0055583 A1 | 3/2018 | Schuh et al. |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2783643 A1 * | 10/2014 ......... A61B 17/2909 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 834 244 | 5/1960 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 201110032444 A | 3/2011 |
| KR | 20130031403 A | 3/2013 |
| WO | WO-82/00611 A1 | 3/1982 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/025818 A1 | 3/2011 |
| WO | WO-2011/027183 A2 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/014621 A1 | 1/2013 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 | 6/2014 |
| WO | WO-2014/094718 | 6/2014 |
| WO | WO-2014/094719 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2015/175200 A1 | 11/2015 |
| WO | WO-2016/083189 A1 | 6/2016 |
| WO | WO-2016/154173 A1 | 9/2016 |
| WO | WO-2016/183054 A1 | 11/2016 |
| WO | WO-01/6189284 A1 | 12/2016 |
| WO | WO-2016/189284 A1 | 12/2016 |
| WO | WO-2017/015599 A1 | 1/2017 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |
| WO | WO-2017/220978 A1 | 12/2017 |
| WO | WO-2018/142112 A1 | 8/2018 |
| WO | WO-2018/162921 A1 | 9/2018 |

OTHER PUBLICATIONS

Abbott, et al., "Design of an Endoluminal NOTES Robotic System," IEEE/RSJ International Conference on Intelligent Robots and Systems, San Diego, CA, pp. 410-416 (2007).

Aesculap Surgical Technologies, Aesculap® Caiman®, Advanced Bipolar Seal and Cut Technology Brochure, 6 pages (retrieved Aug. 31, 2015).

Arata, et al., "Development of a dexterous minimally-invasive surgical system with augmented force feedback capability," IEEE/RSJ International Conference on Intelligent Robots and Systems, pp. 3207-3212 (2005).

Çavuşoğlu, et al., "Laparoscopic Telesurgical Workstation," IEEE Transactions on Robotics and Automation,(15)4:728-739 (1999).

Dachs, et al., "Novel Surgical Robot Design: Minimizing the Operating Envelope Within the Sterile Field," 28th International Conference, IEEE Engineering in Medicine Biology Society, New York, pp. 1505-1508 (2006).

Dario, et al., "Novel Mechatronic Tool for Computer-Assisted Arthroscopy," IEEE Transactions on Information Technology in Biomedicine, 4(1):15-29 (Mar. 2000).

Focacci, et al., "Lightweight Hand-held Robot for Laparoscopic Surgery," IEEE International Conference on Robotics & Automation, Rome, Italy, pp. 599-604 (2007).

(56) References Cited

OTHER PUBLICATIONS

Guthart, et al., "The Intuitive™ Telesurgery System: Overview and Application," IEEE International Conference on Robotics & Automation, San Francisco, CA, pp. 618-621 (2000).
Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).
Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).
International Search Report & Written Opinion dated Feb. 2, 2017 in Int'l PCT Patent Appl. Serial No. PCT/IB2016/001286.
International Search Report & Written Opinion dated Jan. 18, 2013 in Int'l PCT Patent Appl Serial No. PCT/IB2012/053786.
International Search Report dated Jan. 18, 2013 in Int'l PCT Patent Appl Serial No. PCT/IB2012/053786.
International Search Report dated Mar. 23, 2012 in Int'l PCT Patent Appl Serial No. PCT/IB2011/054476.
Ishii, et al., "Development of a New Bending Mechanism and Its Application to Robotic Forceps Manipulator," IEEE International Conference on Robotics & Automation, Rome, Italy, pp. 238-243 (2007).
International Search Report & Written Opinion dated May 23, 2016 in Int'l PCT Patent Appl Serial No. PCT/IB2015/002524.
International Search Report & Written Opinion dated Mar. 30, 2015 in Int'l PCT Patent Appl Serial No. PCT/EP2015/051473.
International Search Report & Written Opinion dated Apr. 26, 2016 in Int'l PCT Patent Appl Serial No. PCT/IB2015/002512.
International Search Report & Written Opinion dated May 24, 2016 in Int'l PCT Patent Appl Serial No. PCT/IB2015/002487.
International Search Report & Written Opinion dated Jun. 10, 2016 in Int'l PCT Patent Appl Serial No. PCT/IB2015/002533.
International Search Report & Written Opinion dated Jun. 13, 2016 in Int'l PCT Patent Appl Serial No. PCT/IB2015/002493.
International Search Report & Written Opinion dated Aug. 25, 2016 in Int'l PCT Patent Appl Serial No. PCT/IB2016/000542.
International Search Report & Written Opinion dated Sep. 2, 2016 in Int'l PCT Patent Appl Serial No. PCT/IB2016/000543.
Kobayashi, et al., "Small Occupancy Robotic Mechanisms for Endoscopic Surgery," International Conference on Medical Image Computing and Computer assisted Interventions, pp. 75-82 (2002).
Mayer, et al., "The Endo[PA]R System for Minimally Invasive Robotic Surgery," IEEE/RSJ International Conference on Intelligent Robots and Systems, Sendai, Japan, pp. 3637-3642 (2004).
Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).
Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).
Peirs, et al., "Design of an advanced tool guiding system for robotic surgery," IEEE International Conference on Robotics & Automation, Taipei, Taiwan, pp. 2651-2656 (2003).
Sallé, et al., "Optimal Design of High Dexterity Modular Mis Instrument for Coronary Artery Bypass Grafting," IEEE International Conference on Robotics & Automation, New Orleans, LA, pp. 1276-1281 (2004).
Seibold, et al., "Prototype of Instrument for Minimally Invasive Surgery with 6-Axis Force Sensing Capability," IEEE International Conference on Robotics & Automation, Barcelona, Spain, pp. 496-501 (2005).
Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).
Stryker®, Endoscopy, Take a Look Around, Ideal Eyes™ FFD122 HD, Articulating Laparoscope Brochure, 2 pages (2009).
Swiss Search Report dated Jun. 4, 2012 in Swiss Patent Application No. CH 00702/12.
Tavakoli, et al., "Force Reflective Master-Slave System for Minimally Invasive Surgery," IEEE/RSJ International Conference on Intelligent Robots and Systems, Las Vegas, NV, pp. 3077-3082 (2003).
Taylor, et al., "Steady-Hand Robotic System for Microsurgical Augmentation," The International Journal of Robotics Research, 18(12):1201-1210 (1999).
www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.
Yamashita, et al., "Development of Endoscopic Forceps Manipulator Using Multi-Slider Linkage Mechanisms," The 1st Asian Symposium on Computer Aided Surgery-Robotic and Image-Guided Surgery, Ibaraki, Japan, 4 pages (2005).
Zeus, "Robotic Surgical System" available at http://al-laboutroboticsurgery.com/zeusrobot.html.
Communication Relating to the Results of the Partial International Search dated May 28, 2019 in Int'l PCT Patent Appl. Serial No. PCT/IB2019/050961.
International Search Report & Written Opinion dated Jul. 10, 2018 in Int'l PCT Patent Appl. Serial No. PCT/IB2018/053272.

* cited by examiner

Figure 28
Figure 29
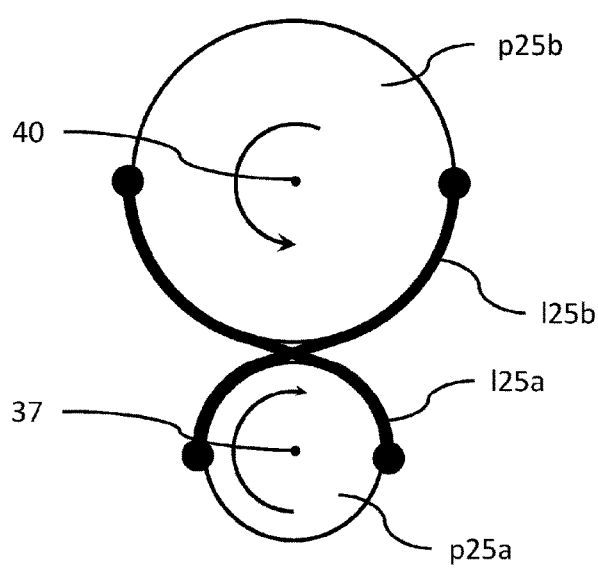
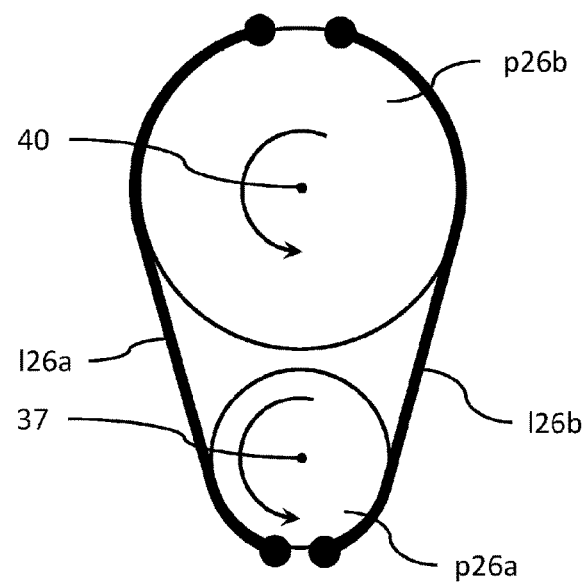

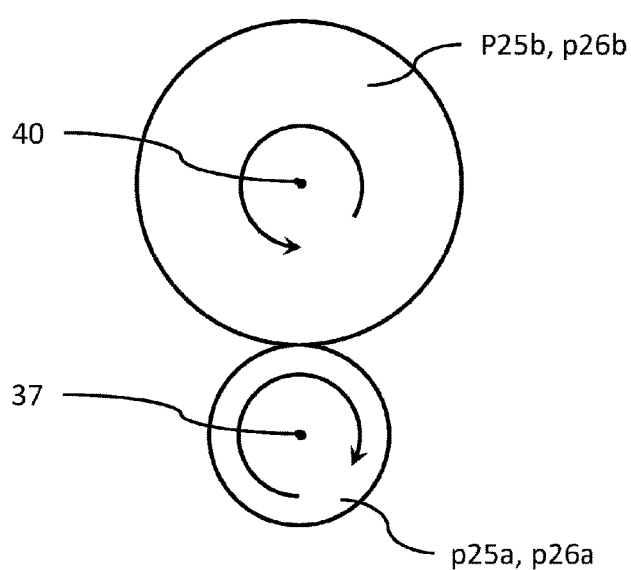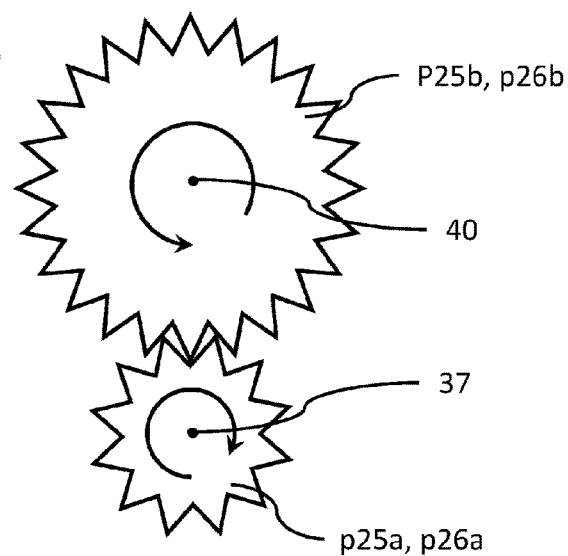

ARTICULATED HANDLE FOR MECHANICAL TELEMANIPULATOR

FIELD OF THE INVENTION

The present invention relates to the field of remotely actuated mechanical systems, more particularly to endoscopic mechanisms, and most particularly to remotely actuated endoscopic surgical instruments. More specifically, this invention relates to articulated handle mechanisms used to control surgical instruments such as graspers, dissectors, and scissors, wherein the orientation of end-effectors in relation to the instrument shaft is able to be controlled. This mechanism is also adapted for any suitable remote actuated application requiring dexterous manipulation with high stiffness and precision such as, but in no way limited to, assembly manipulation, manipulation in narrow places, manipulation in dangerous or difficult environments, and manipulation in contaminated or sterile environments.

BACKGROUND OF THE INVENTION

Open surgery is still the standard technique for most surgical procedures. It has been used by the medical community for several decades and consists of performing the surgical tasks through a long incision in the abdomen, through which traditional surgical tools are inserted. However, due to the long incision, this approach is extremely invasive for the patients, resulting in substantial blood loss during the surgery and long and painful recovery periods at the hospital.

In order to reduce the invasiveness of open surgery, laparoscopy, a minimally invasive technique, was developed. Instead of a single long incision, four to five small incisions are made in the patient through which appropriately sized surgical instruments and endoscopic cameras are inserted. Because of the low invasiveness, this technique reduces blood loss and shortens hospital stays and pain. When performed by experienced surgeons, this technique can attain clinical outcomes similar to open surgery. However, despite the above-mentioned advantages, laparoscopy requires extremely advanced surgical skills to manipulate the rigid and long instrumentation. The entry incision acts as a point of rotation, decreasing the surgeon's freedom for positioning and orientating the instruments inside the patient. The movements of the surgeon's hand about this incision are inverted and scaled-up relative to the instrument tip ("fulcrum effect"), which removes dexterity, sensibility and magnifies the tremors of the surgeon's hands. In addition, these long and straight instruments force surgeons to work in a uncomfortable posture, which can be tremendously tiring during several hours of operation and result in stress and discomfort for hands, arms and body. Therefore, due to these drawbacks of laparoscopic instrumentation, these minimally invasive techniques are mainly limited to use in simple surgeries, while only a small minority of surgeons is able to use them in complex procedures.

To overcome these limitations, surgical robotic systems were developed to provide an easier-to-use approach to complex minimally invasive surgeries. By means of a computerized robotic interface, these systems enable the performance of remote laparoscopy wherein the surgeon sits at a console manipulating two master manipulators to perform the operation through several small incisions. Like laparoscopy, the robotic approach is also minimally invasive, bringing several advantages over open surgery in terms of reduced pain, blood loss, and recovery time. In addition, it also offers better ergonomy for the surgeon compared to open and laparoscopic techniques. However, although being technically easier, robotic surgery brings several negative aspects. A major disadvantage of these systems is related to the extremely high complexity of existing robotic devices, which are composed of complex mechanical and electronic systems, leading to huge costs of acquisition and maintenance, which are not affordable for the majority of surgical departments worldwide. Another drawback of these systems comes from the fact that current surgical robots are very large, competing for precious space within the operating room environment and significantly increasing preparation time. Access to the patient is thus impaired, which, together with a lack of force-feedback, raises safety concerns.

WO9743942, WO9825666 and US2010011900 disclose a robotic tele-operated surgical instrument, designed to replicate a surgeon's hand movements inside the patient's body. By means of a computerized, robotic interface, it enables the performance of remote laparoscopy wherein the surgeon sits at a console manipulating two joysticks to perform the operation through several small incisions. However, this system does not have autonomy or artificial intelligence, being essentially a sophisticated tool fully controlled by the surgeon. The control commands are transmitted between the robotic master and robotic slave by a complex computer-controlled mechatronic system, which is extremely costly to produce and maintain and difficult to use for the hospital staff.

WO2013014621 describes a mechanical telemanipulator for remote manipulation with a master-slave configuration, comprising a slave manipulator driven by a kinematically equivalent master manipulator and a mechanical transmission system such that each part of the slave manipulator mirrors the movement of each corresponding part of the master manipulator. Therefore, this system allows surgeons to perform surgical procedures by directly manipulating a control handle in the proximal part of the mechanical telemanipulator while their movements are replicated (scaled down or not) by an articulated instrument that can reach the abdominal cavity of the patient through small incisions or trocars. Although the mechanical transmission system is well adapted to the device, the kinematic model and transmission topology of the handle were not optimized, forcing surgeons to move their hands in non-ergonomic ranges of motion and limiting the amount of gripping force that can be generated at the instrument's end-effector.

Accordingly, an aim of the present invention is to provide a mechanical telemanipulator handle mechanism with a new configuration, which is able to deliver higher gripping forces to the instrument's end-effector.

Another aim of the present invention is to provide a mechanical telemanipulator handle mechanism with a more ergonomic range of motion for the surgeon's hands.

SUMMARY OF THE INVENTION

Theses aims and other advantages are achieved by a new articulated handle mechanism, designed to be used at the proximal extremity of a mechanical telemanipulator. This mechanical telemanipulator is intended to control surgical instruments, in the form of, for example, a dissector, scissor or grasper, with articulated distal end-effectors. These distal articulations of the end-effectors are able to (1) operate the surgical instrument in order to accomplish its "open/close" function (for example, grasping or cutting) and (2) provide orientation motions between the end effector and the instrument shaft. The handle corresponds to the distal degreesof-freedom of the master manipulator and the end-effector corresponds to the distal degrees-of-freedom of the slave manipulator. The mechanical telemanipulator further comprises a mechanical transmission system arranged to kinematically connect all the master degrees-of-freedom to the equivalent end-effector degrees-of-freedom such that the end-effector replicates the movements of the handle.

In order to deliver higher gripping forces to the instrument's end-effector and to provide a more ergonomic range of motion for the surgeon's hands, the handle comprises an amplification system configured to act on the two distal degrees-of-freedom. With this amplification system, the angular relation between master and slave degrees-of-freedom is changed in some degrees of freedom. While for general degrees-of-freedom of the mechanical telemanipulator there is a "1 to 1" angular relation between a master joint and the equivalent slave joint, the angular relation between the two distal articulations of the handle and the two distal articulations of the end-effector is modified only for the "open/close" function, while the angular relation for orientation motions remains "1 to 1". For the "open/close" function, the angular relation can be linearly amplified (for instance, "2 to 1" or "3 to 1") or non-linearly amplified, depending on the invention's embodiment.

BRIEF DESCRIPTION OF FIGURES

The invention will be better understood according to the following detailed description of several embodiments with reference to the attached drawings, in which:

FIGS. 28 through 35 show motion transmission from first to the second amplification pulleys by various mechanical means according to various embodiments of the current invention.

DETAILED DESCRIPTION OF THE INVENTION

Figure 1:
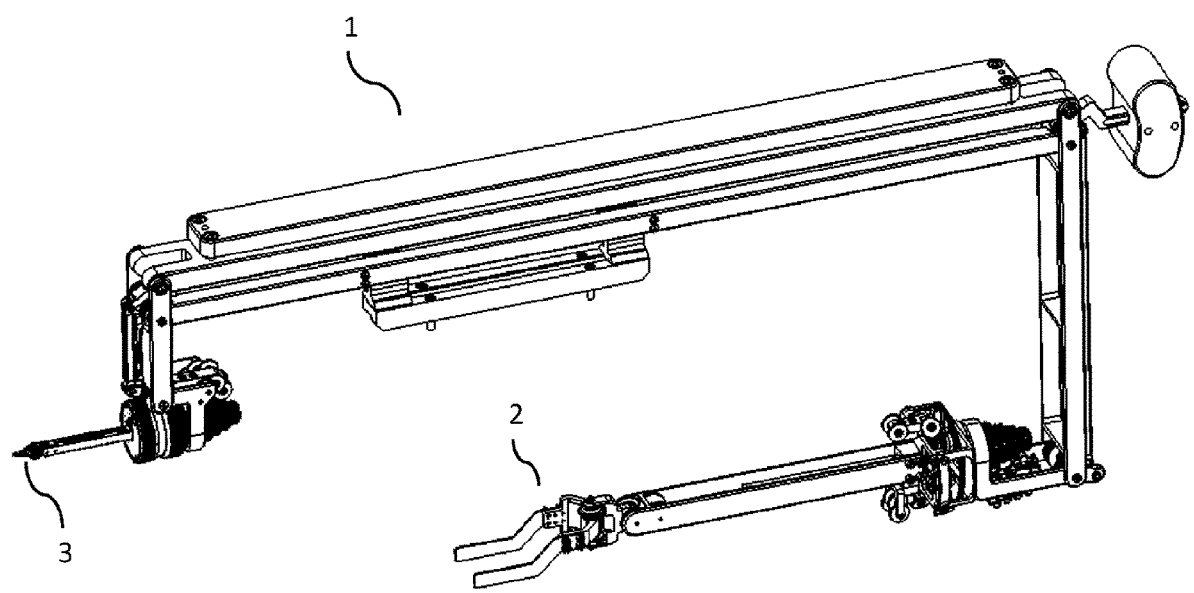
FIG. 1 shows a perspective view of a mechanical telemanipulator according to an embodiment of the current invention.

The articulated handle 2, according to an embodiment of the present invention, is intended to be used in a mechanical telemanipulator 1, like the one shown in FIG. 1.

One of the key features of this type of mechanical telemanipulator 1 lies in its master-slave architecture, which enables a natural replication of the user hand movements, on a proximal handle 2, by a distal end-effector 3 on a remote location.

Figure 2:
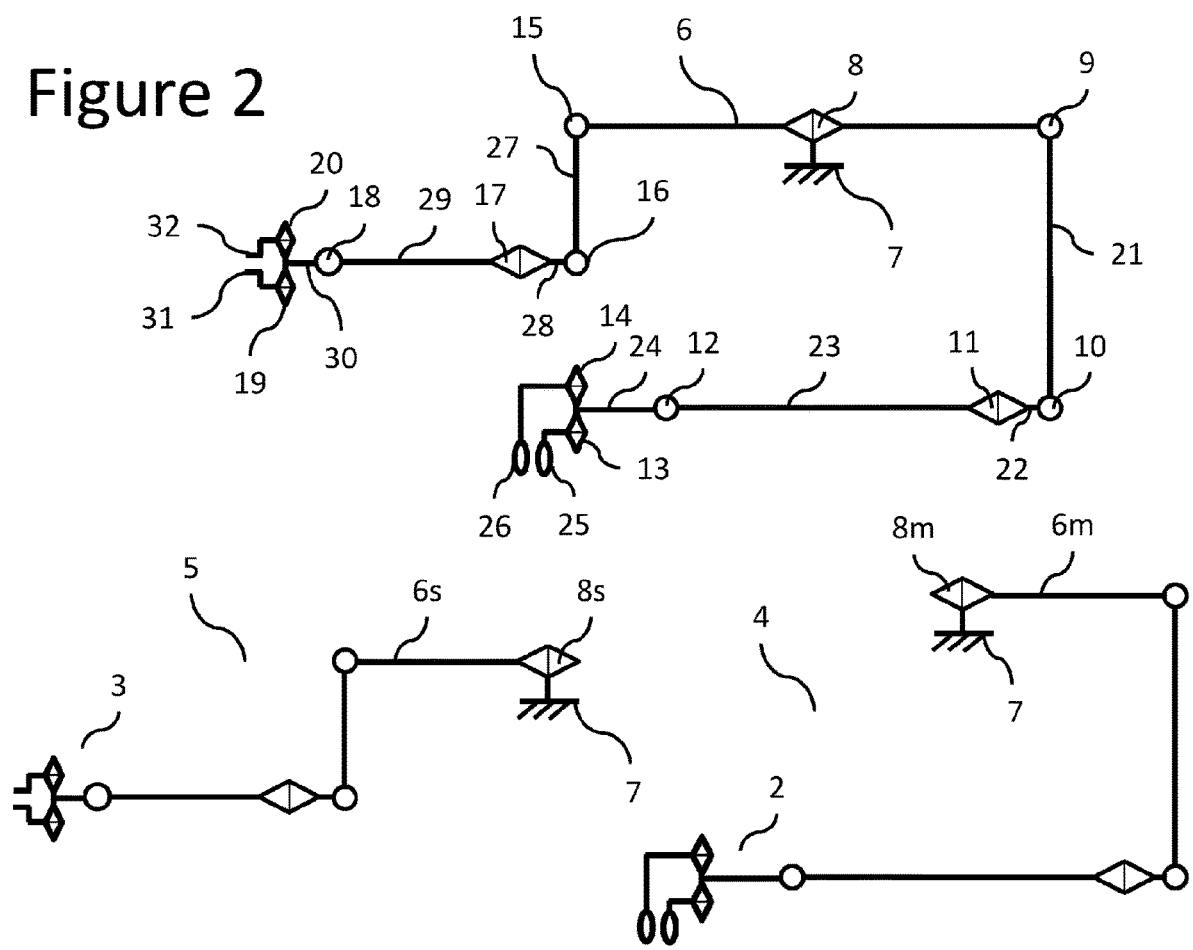
FIG. 2 shows a schematic view of a mechanical telemanipulator according to an embodiment of the invention disclosed in WO2013014621.

According to FIG. 2, the mechanical telemanipulator 1 (according to an embodiment of the current invention and the invention disclosed in WO2013014621) may comprise: i) a master manipulator 4 having a corresponding number of master links 21, 22, 23, 24, 25, 26 interconnected by a plurality of master joints 9, 10, 11, 12, 13, 14, a ii) a handle 2 for operating the mechanical telemanipulator 1, connected to the distal end of the master manipulator 4, iii) a slave manipulator 5 having a number of slave links 27, 28, 29, 30, 31, 32 interconnected by a plurality of slave joints 15, 16, 17, 18, 19, 20; and iv) an end-effector 3 (instrument/tool or a gripper/holder) connected to the distal end of the slave manipulator 5. More particularly, the kinematic chain formed by the plurality of articulated slave links 27, 28, 29, 30, 31, 32 and corresponding slave joints 15, 16, 17, 18, 19, 20 of the slave manipulator 5, may be substantially identical to the kinematic chain formed by the plurality of articulated master links 21, 22, 23, 24, 25, 26 and corresponding master joints 9, 10, 11, 12, 13, 14 of the master manipulator 4.

Referring still to FIG. 2, the master manipulator 4 and the slave manipulator 5 are connected to each other by a connecting link 6. This connecting link 6 is connected to a ground 7 by a first telemanipulator joint 8. This first telemanipulator joint 8 can be decomposed in a master joint 8m and slave joint 8s, which can respectively be considered as the first proximal joints of the master manipulator 4 and the slave manipulator 5. In the same way, the connecting link 6 can be decomposed in a master link 6m and slave link 6s, which can respectively be considered as the first proximal links of the master manipulator 4 and the slave manipulator 5.

Figure 3:
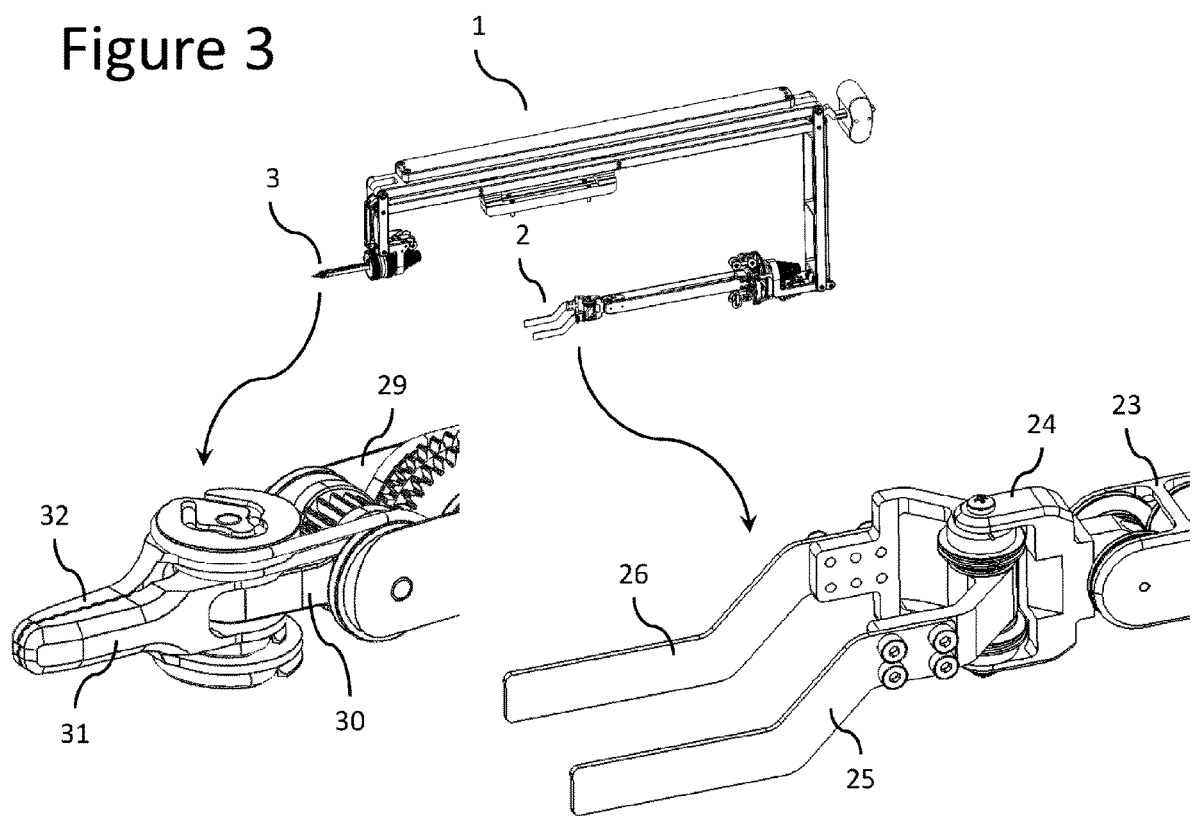
FIG. 3 shows a perspective view of a mechanical telemanipulator comprising an articulated end-effector and an articulated handle according to an embodiment of the invention disclosed in WO2013014621.

The configuration of the mechanical telemanipulator can also be described by considering the end-effector 3 to be part of the slave manipulator 5 and the handle 2 to be part of the master manipulator 4. In a broader sense, the links and joints composing the end-effector can be considered distal slave links and joints, while the links and joints composing the handle can be considered distal master links and joints. FIG. 3 shows a close-up view of the proximal handle 2 and the distal end-effector 3, with their respective moving links (according to an embodiment of the invention disclosed in WO2013014621).

Figure 4:
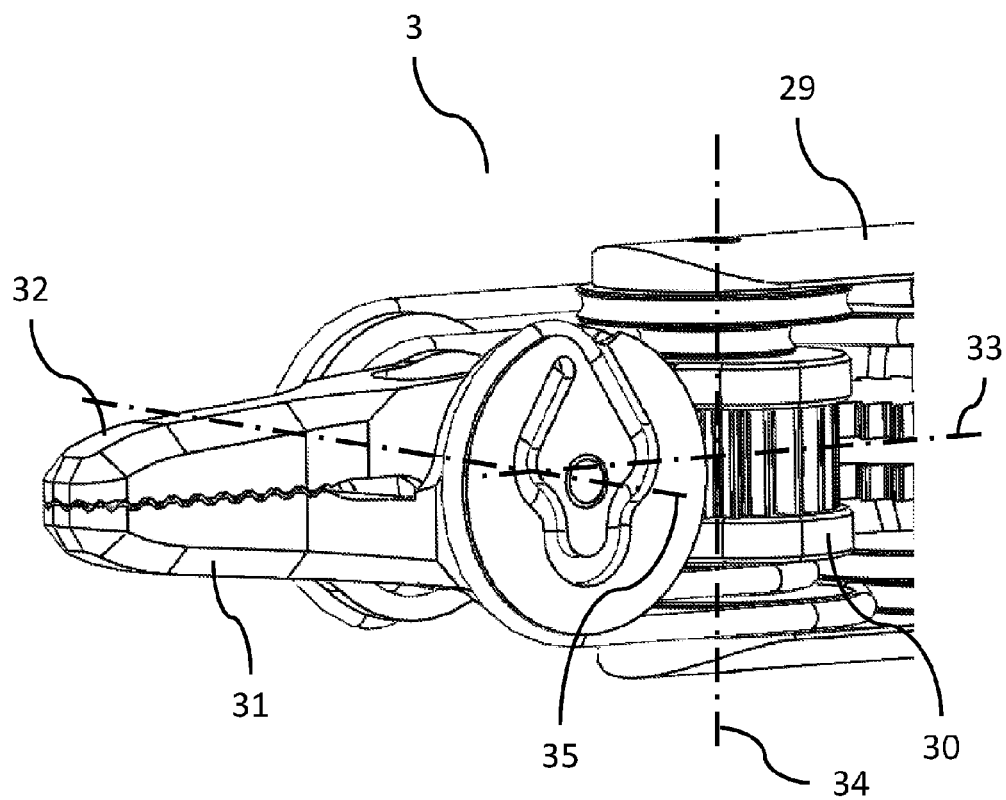
FIG. 4 shows a perspective view of a distal end-effector of the mechanical telemanipulator according to an embodiment of the current invention and the invention disclosed in WO2013014621.
Figure 5:
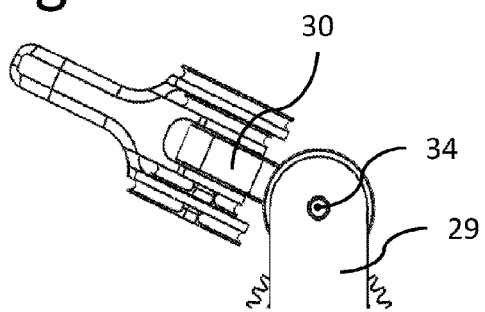
FIG. 5 shows a distal end-effector of the perspective of FIG. 4 in a first active position.
Figure 6:
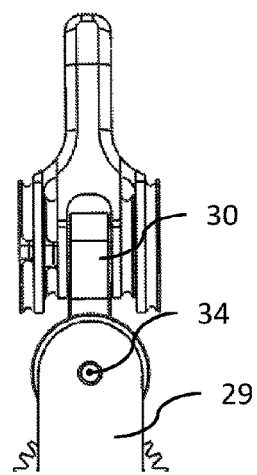
FIG. 6 shows a distal end-effector of the perspective of FIG. 4 in a second active position.
Figure 7:
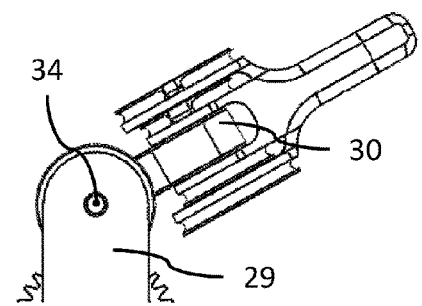
FIG. 7 shows a distal end-effector of the perspective of FIG. 4 in a third active position.

Referring to FIG. 4, the end-effector 3 is connected to the distal extremity of the slave link 29 by a proximal joint, which allows the rotation of the proximal end-effector link 30 by the proximal axis 34 in such a manner that the orientation of the proximal end-effector link 30 with respect to the main axis 33 of the slave link 29 can be changed. The distal end-effector links 31, 32 are pivotally connected to the proximal end-effector link 30 by two distal joints, having coincident axes of rotation, which are represented by the distal axis 35. This distal axis 35 is substantially perpendicular and non-intersecting with the proximal axis 34 and substantially intersects the main axis 33 of the slave link 29. FIGS. 5 to 7 show the end-effector 3 with different angular displacements at the proximal end-effector link 30.

Figure 8:
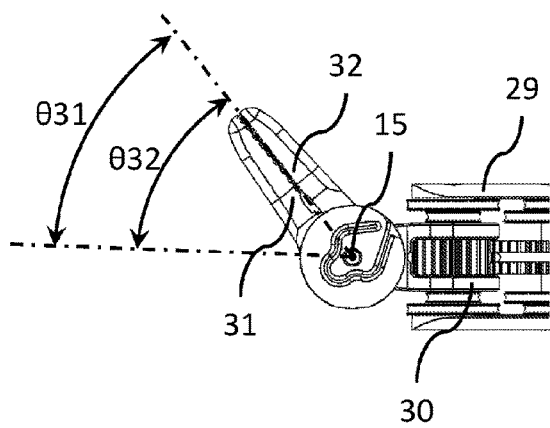
FIG. 8 shows a distal end-effector of the perspective of FIG. 4 in a fourth active position.
Figure 9:
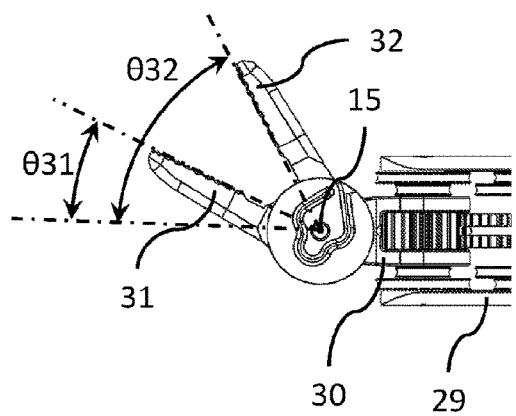
FIG. 9 shows a distal end-effector of the perspective of FIG. 4 in a fifth active position.

By actuating the two distal joints, the two distal end-effector links 31, 32 can be angulated over the distal axis 35, with respect to the plane containing the main axis 33 and the distal axis 35, by the angles $\theta 31$, $\theta 32$. Consequently, by the combination of rotations $\theta 31$, $\theta 32$, it is possible to operate the surgical instrument, in order to provide orientation motions between the end effector and the slave link 29 (FIG. 8) and to accomplish its "open/close" function (FIG. 9).

The mechanical telemanipulator 1 further comprises mechanical transmission systems arranged to kinematically connect the slave manipulator 5 with the master manipulator 4 such that the movement (angle of joint) applied on each master joint of the master manipulator 4 is reproduced by the corresponding slave joint of the slave manipulator 5.

Figure 10:
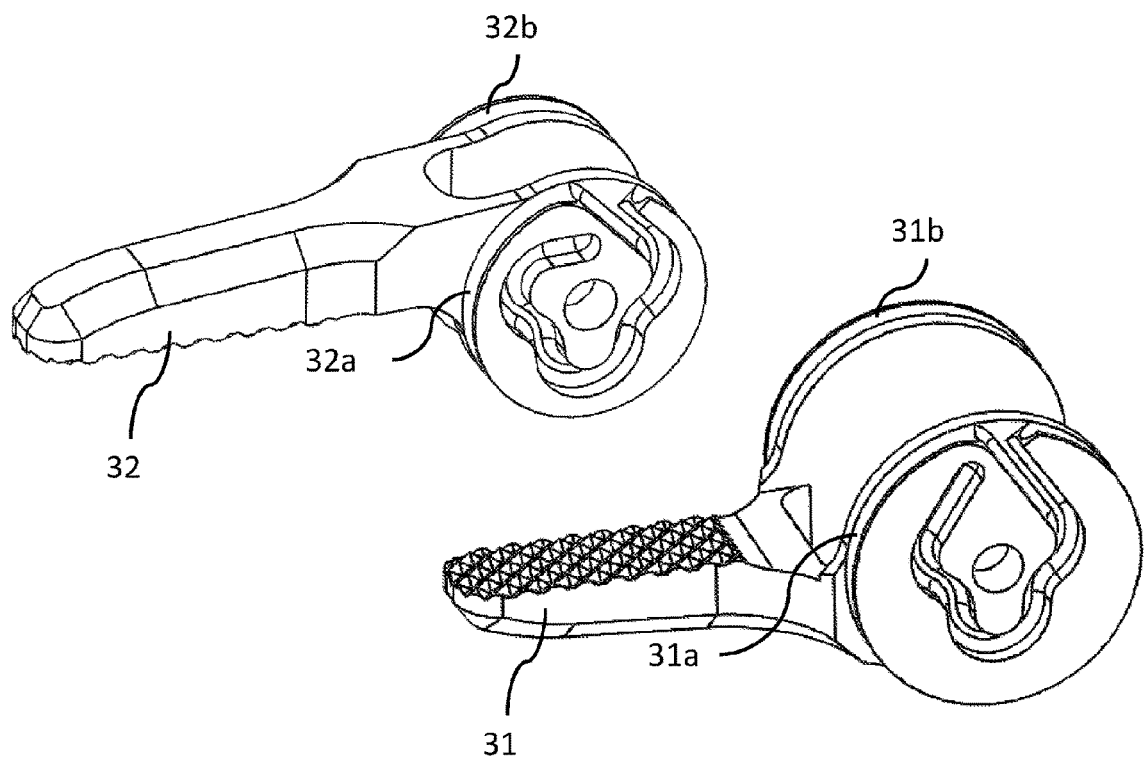
FIG. 10 shows a perspective views of two distal end-effector links.

For each degree of freedom of the mechanical telemanipulator 1, different types of mechanical transmissions can be used. In order to minimize the system's overall friction and inertia, while increasing "back-drivability" and stiffness, the mechanical transmission between the majority of the master and slave joints is essentially in the form of pulley-routed flexible elements, where each driven pulley of the slave joint is connected to the respective driving pulley of the master joint, by a multi-stage closed cable loop transmission. As can be seen in FIG. 4, the distal end-effector members 31, 32 are operatively connected to flexible members so that they can be independently rotated in both directions along the distal axis 35. The contact between the flexible elements and the distal end-effector elements is made in the circular grooved surfaces 31a, 31b, 32a, 32b (FIG. 10), which have a pulley-like geometry, forming the pulleys p31 and p32.

Figure 11:
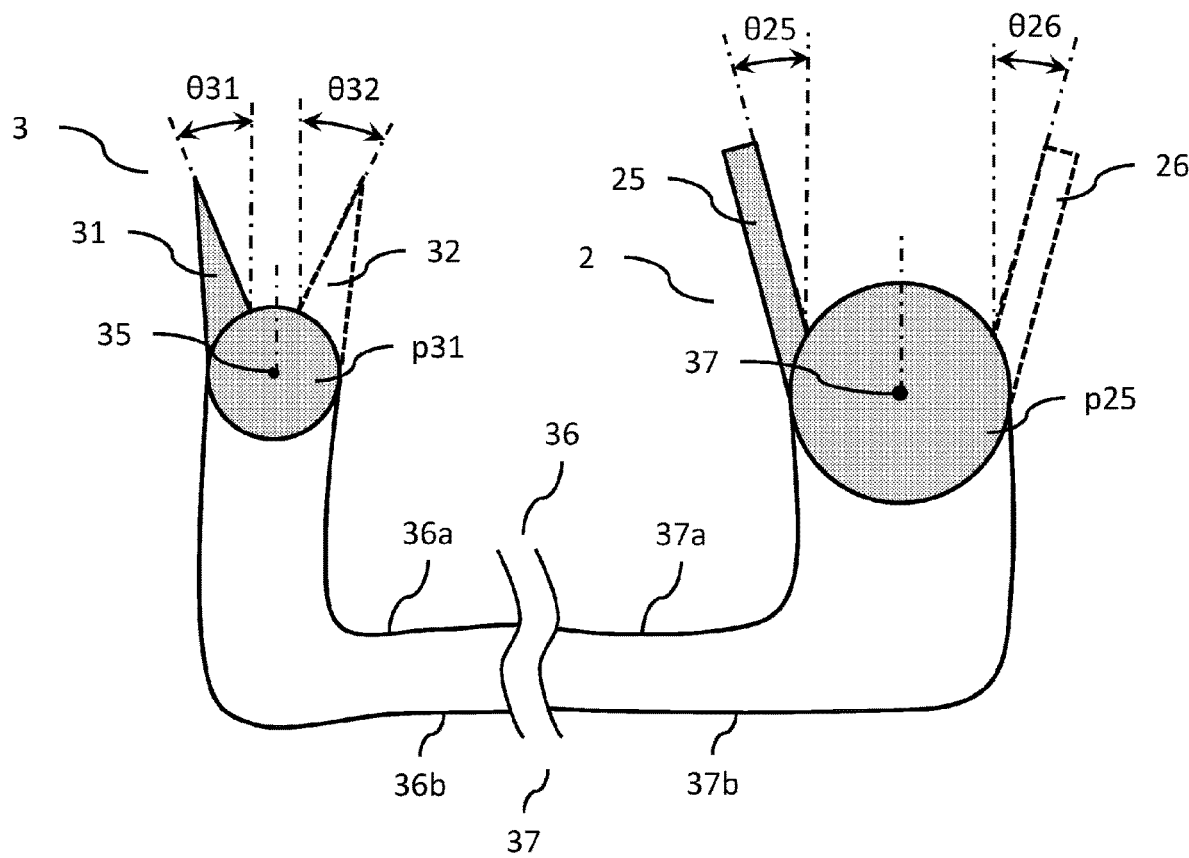
FIG. 11 shows the transmission topology for the two distal end-effector links, during an "opened" configuration, according to an embodiment of the invention disclosed in WO2013014621.

FIG. 11 shows the working principle of this actuation for the case of transmitting the rotations $\theta 25$, $\theta 26$ from the driving pulleys p25 (shaded in FIG. 11) and p26 (not visible in FIG. 11) around the axis 37, on the proximal handle 2, to the rotations $\theta 31$, $\theta 32$ of the driven pulleys p31 (shaded in FIG. 11) and p32 (not visible in FIG. 11) around the axis 35, on the end-effector 3. The flexible element 36 is composed by two different segments, 36a, 36b, which form a closed cable loop between the driven pulley p31 of the end-effector link 31 and the driving pulley p25 of the handle link 25. The flexible element 37 (coincident with flexible element 36 in FIG. 11) is composed by two different segments 37a, 37b, which form a closed cable loop between the driven pulley p32 end-effector link 32 (dashed in FIG. 11) and the driving pulley p26 of the handle link 26 (dashed in FIG. 11). These flexible elements 36, 37 connect the driving pulley 25p to the driven pulley 31p and the driving pulley 26p to the driven pulley 32p so that $\theta 31=\theta 25$ and $\theta 32=\theta 26$.

Figure 12:
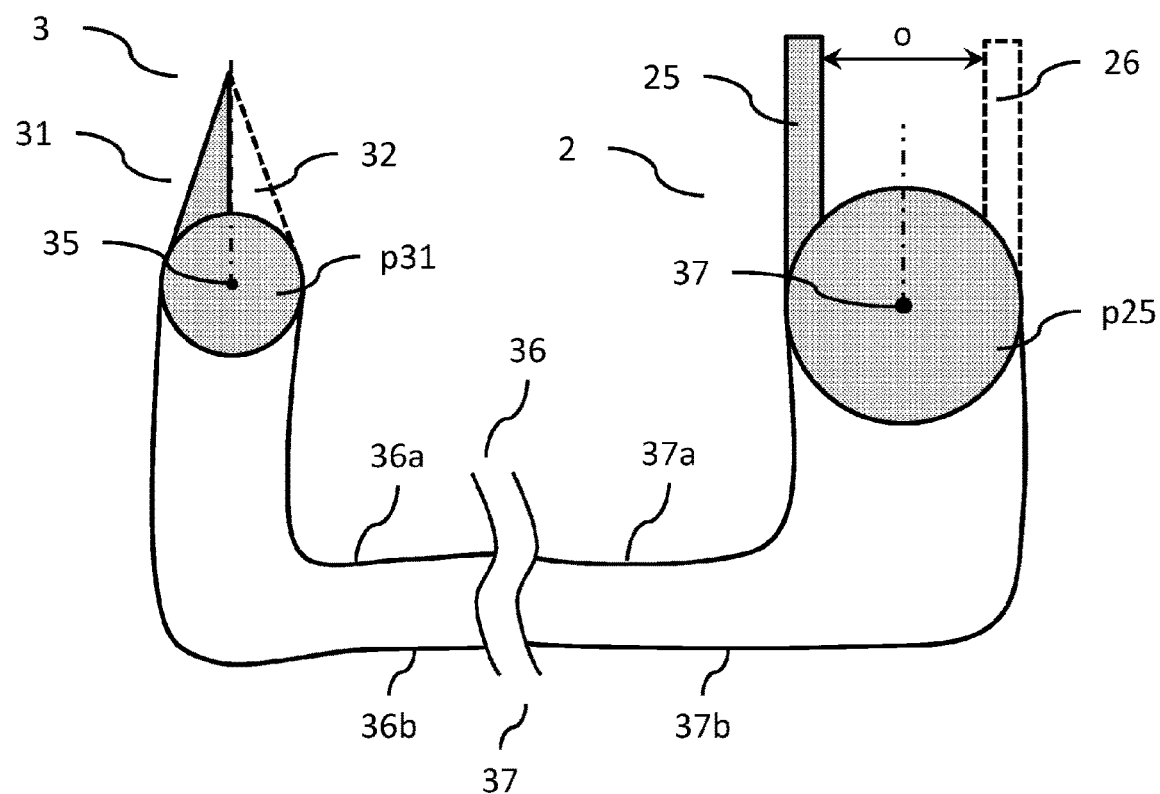
FIG. 12 shows the transmission topology for the two distal end-effector links, during an "closed" configuration, according to an embodiment of the invention disclosed in WO2013014621.
Figure 13:
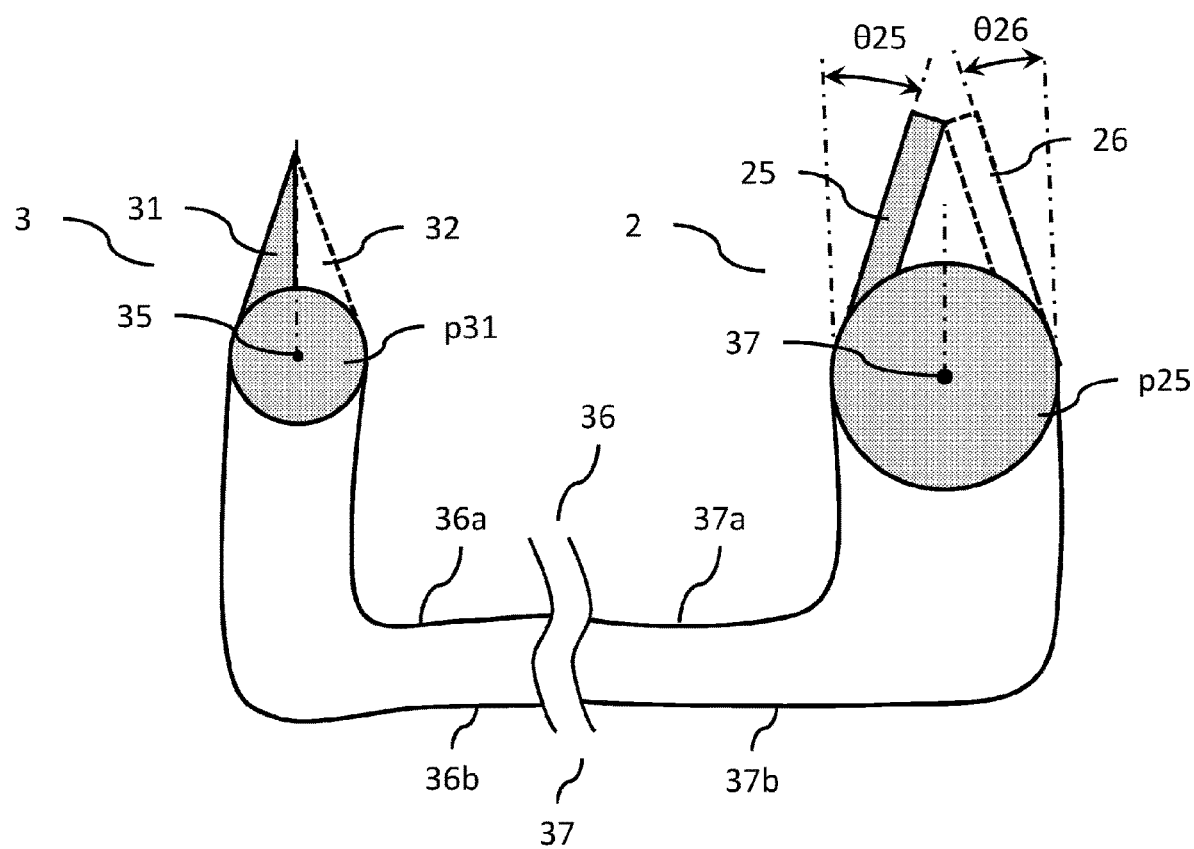
FIG. 13 shows the transmission topology for the two distal end-effector links, during an "force-applying" configuration, according to an embodiment of the invention disclosed in WO2013014621.
Figure 14:
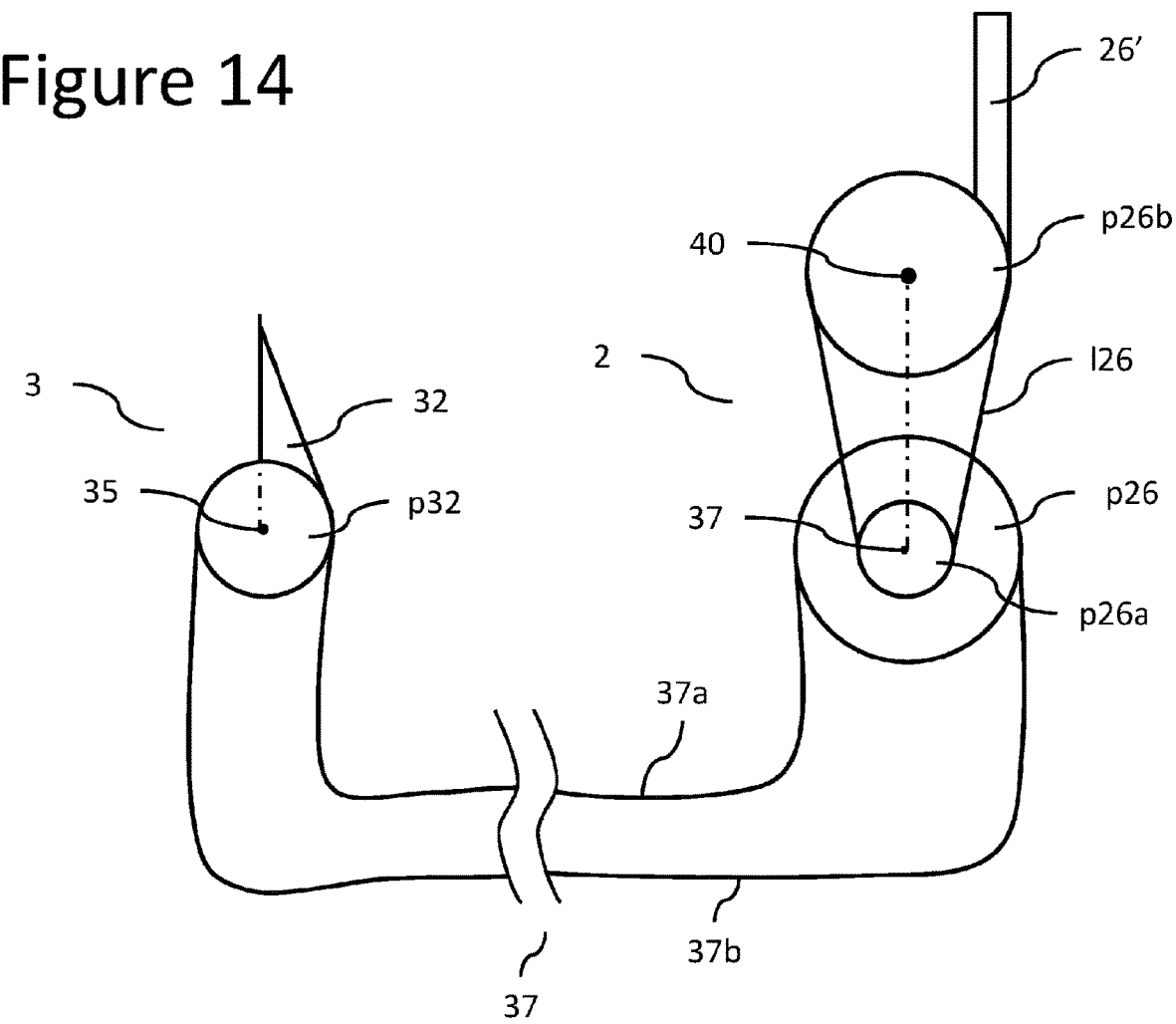
FIG. 14 shows the transmission topology for a first distal end-effector link, according to an embodiment of the current invention.

FIG. 12 show the configuration where $\theta 25=\theta 26=0$. In this case, $\theta 31=\theta 32=0$, and the end-effector remains closed while no gripping force is being applied between the end-effector links 31 and 32. To increase the gripping force of the end-effector 3, the handle links 25 and 26, which are parallel but separated by an offset o (FIG. 12), need to be further moved towards each other, by the angles $\theta 25$, $\theta 26$ (FIG. 13). These further movements stretch the segments 36a and 37b, which increases the force of the end-effector link 31 against the end-effector link 32. However, as can be seen in FIG. 13, the amount of griping force that can be achieved in this configuration, which is related to the rotation angles $\theta 25$, $\theta 26$, is geometrically limited by the physical collision between the handle links 25 and 26.

An articulated handle 2 able to overcome the above mentioned limitation is shown, inter alia, in FIGS. 14 to 27, according to different embodiments of the present invention. It comprises an amplification system that is introduced at the handle 2 level so that i) the rotations $\theta 25$, $\theta 26$ are not physically limited (or the limitation allows for broader ranges of $\theta 25$ and $\theta 26$) and ii) there is an amplification factor $\alpha$ between the rotation of the handle links 25 and 26 and the end-effector links 31 and 32, so that, when the end-effector links 31 and 32 are already in contact, the same movement of the handle links 25 and 26 will create a higher stretch on the segments 36a and 37b, which therefore increases the gripping force at the end-effector (compared with the handle mechanisms shown in FIGS. 11 to 13).

Just like in the previous systems shown in FIGS. 11 to 13 (embodiments of WO2013014621), the driven pulley p32 is connected to the driving pulley p26 by the flexible element 37. However, in this solution, instead of being rigidly attached to the handle link 26, the driving pulley p26 is rigidly attached to a first amplification pulley p26a, which is connected to a second amplification pulley p26b by a handle flexible element 126. This second amplification pulley p26b is able to rotate around a second axis 40 and is rigidly attached to the replacement handle link 26', which replaces the handle link 26 from the system shown in FIGS. 11 to 13. The ratio between the diameters of second amplification pulley p26b and the first amplification pulley p26a correspond to the amplification factor α of the handle 2, which corresponds also to the ratio between the angle θ32 of the end-effector link 32 and the angle θ26' of the replacement handle link 26' ($\theta 32/\theta 26'=\emptyset p26b/\emptyset p26a=\alpha$).

Figure 15:
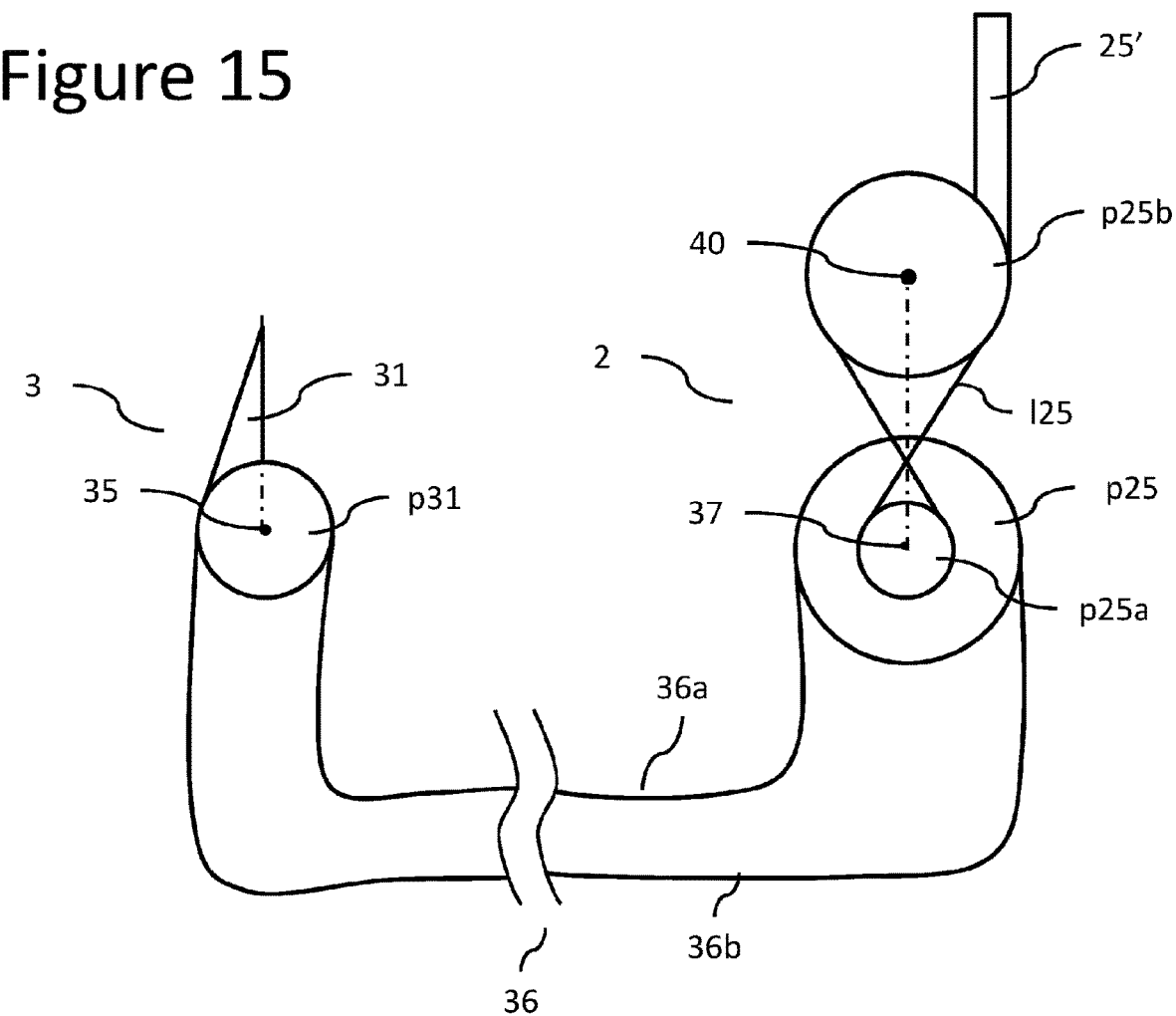
FIG. 15 shows the transmission topology for a second distal end-effector link, according to an embodiment of the current invention.

FIG. 15 shows the previously described system applied to the actuation of the end-effector link 31. Just like in the previous systems shown in FIGS. 11 to 13, the driven pulley p31 is connected to the driving pulley p25 by the flexible element 36. However, in this solution, instead of being rigidly attached to the handle link 25, the driving pulley p25 is rigidly attached to a first amplification pulley p25a, which is connected to a second amplification pulley p25b by a handle flexible element 125. This second amplification pulley p25b is able to rotate around a second axis 40 and is rigidly attached to the replacement handle link 25', which replaces the handle link 25 from the system shown in FIGS. 13 to 15. The ratio between the diameters of second amplification pulley p25b and the first amplification pulley p25a correspond to the amplification factor α of the handle 2, which corresponds also to the ratio between the angle θ31 of the end-effector link 31 and the angle θ25' of the replacement handle link 25' ($\theta 31/\theta 25'=\emptyset p25b/\emptyset p25a=\alpha=\theta 32/\theta 26'=\emptyset p26b/\emptyset p26a$).

Figure 16:
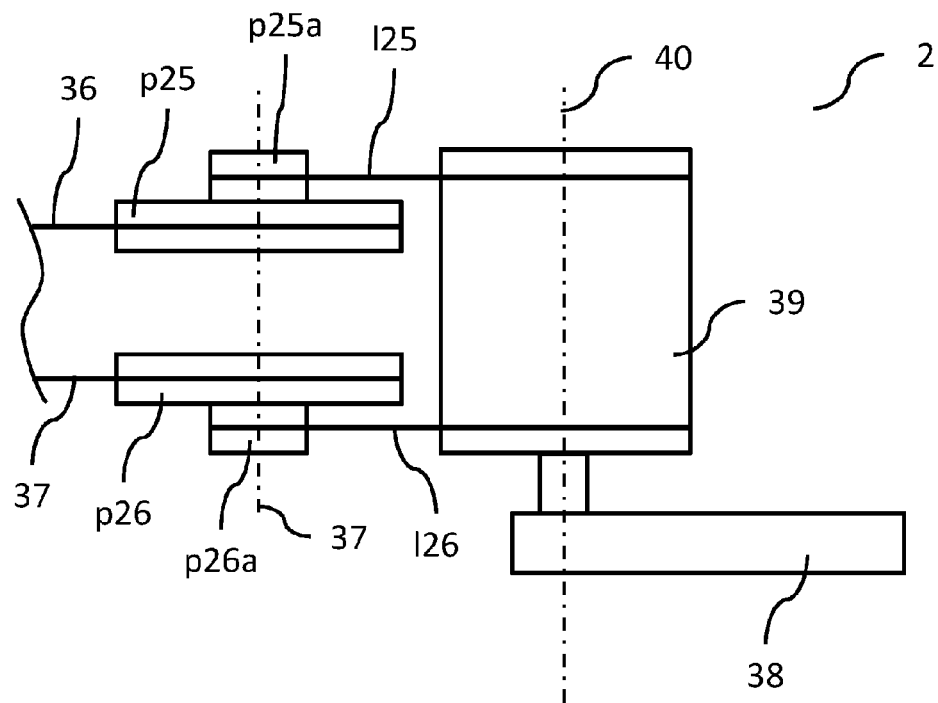
FIG. 16 shows a schematic side view of an articulated handle, according to an embodiment of the current invention.
Figure 17:
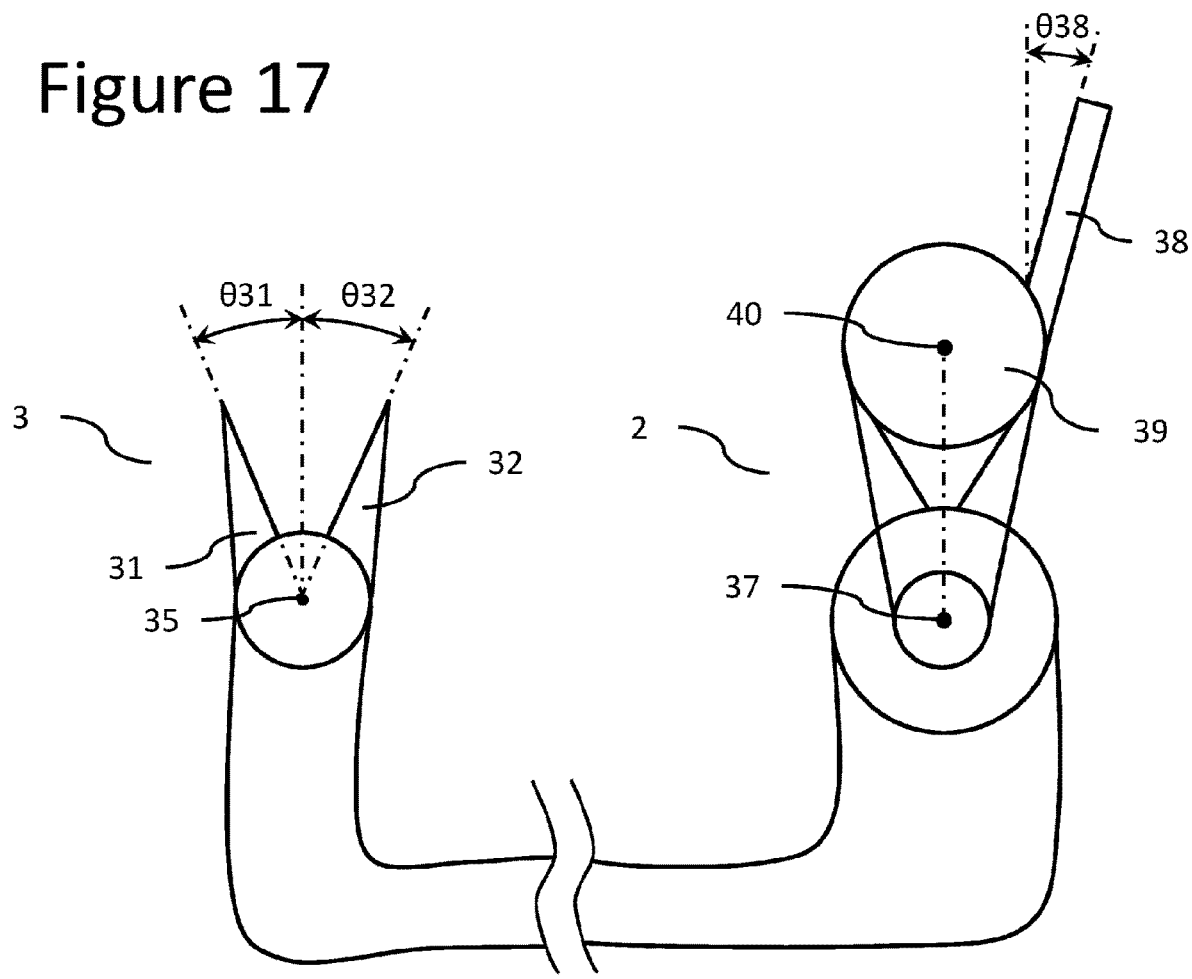
FIG. 17 shows the transmission topology for two distal end-effector links, during an "opened" configuration, according to an embodiment of the current invention.

FIG. 16 shows the side view of an embodiment of the current invention where the replacement handle link 25' and replacement handle link 26' are merged in a single replacement handle link 38 and the second amplification pulley p25b and the second amplification pulley p26b are merged in a single second amplification pulley 39. As can be seen in FIG. 17, this solution enables to simultaneously trigger the actuation to both the end-effector link 31 and end-effector link 32, with an amplification factor α ($\theta 38.\alpha=\theta 25=\theta 26$).

Figure 18:
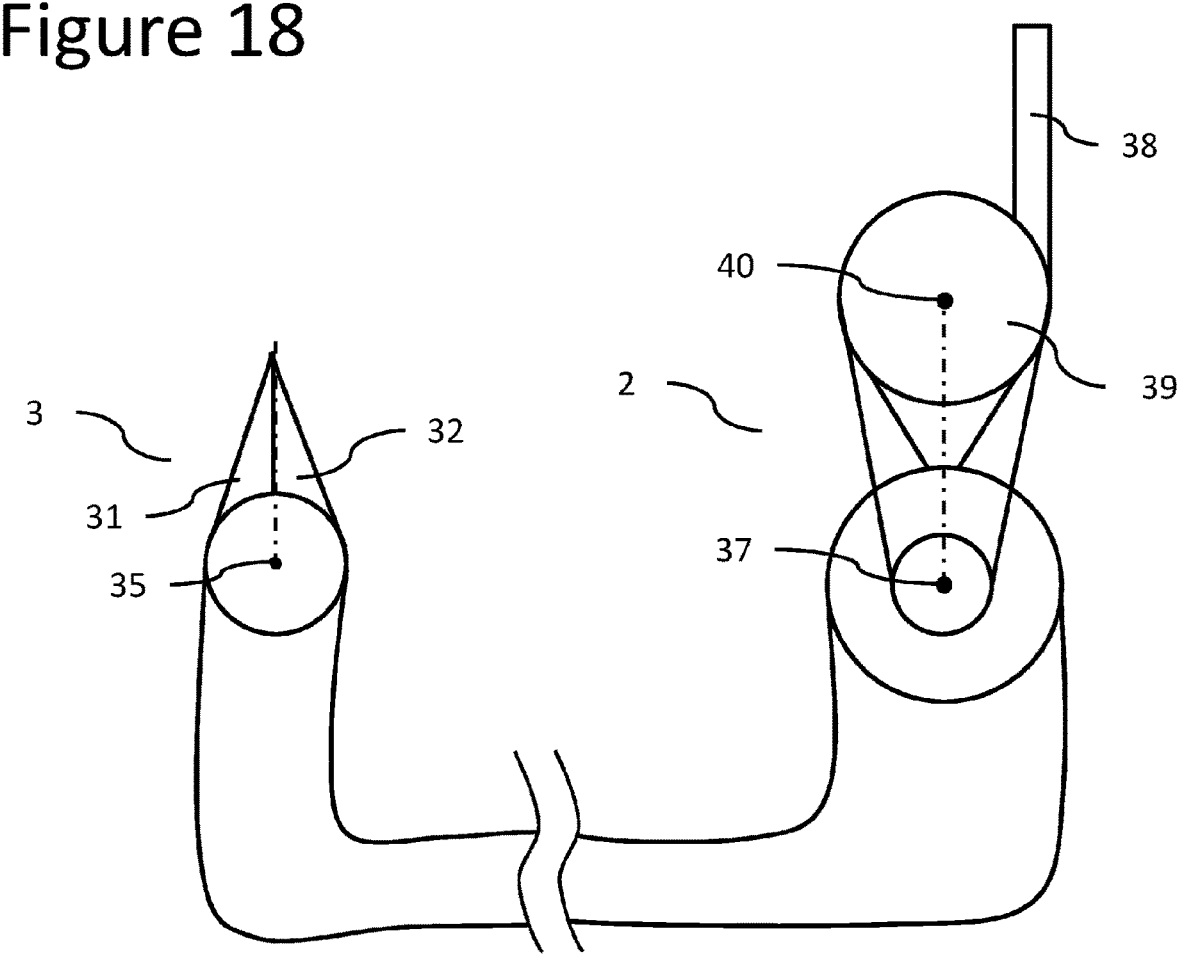
FIG. 18 shows the transmission topology for two distal end-effector links, during an "closed" configuration, according to an embodiment of the current invention.
Figure 19:
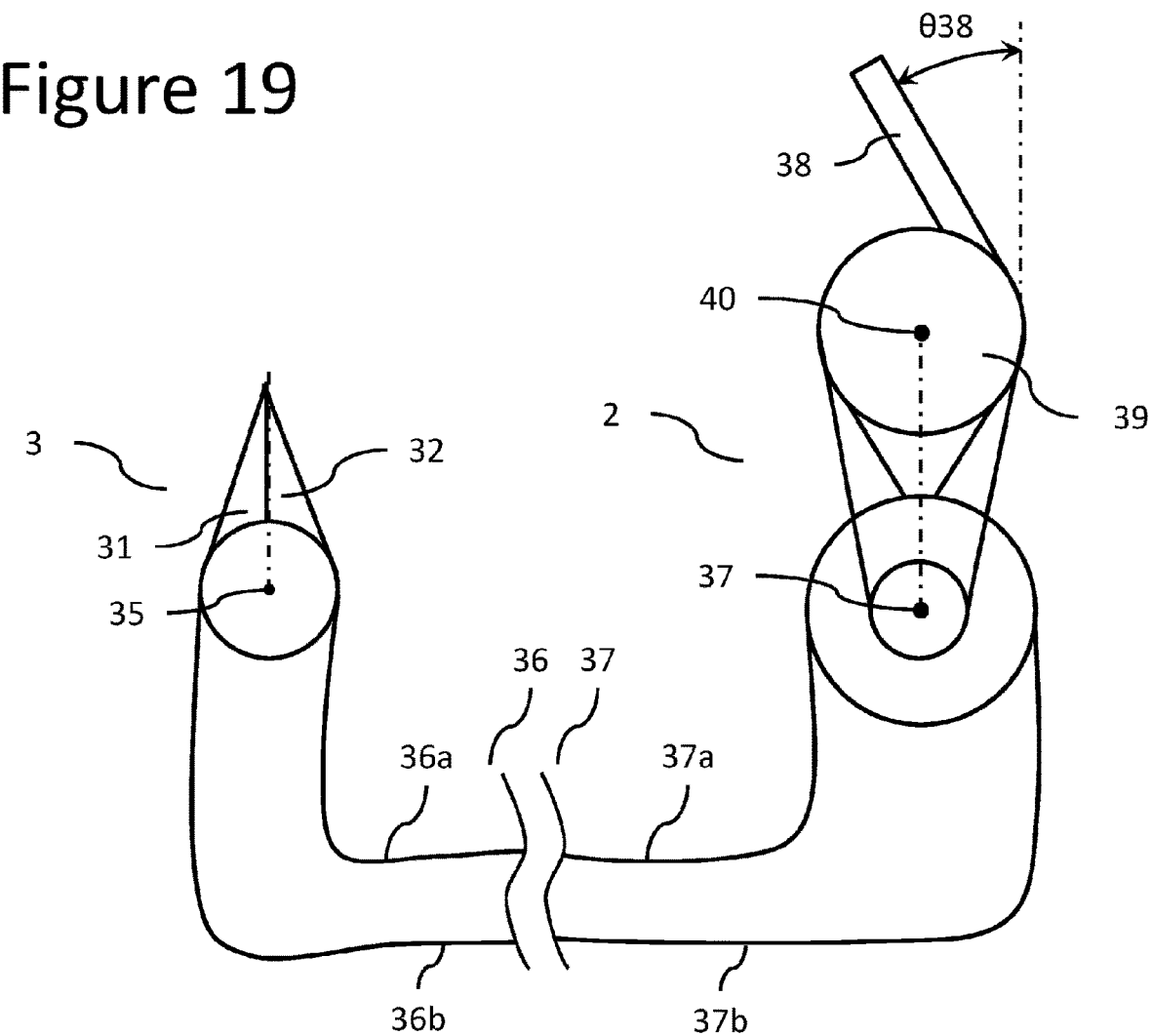
FIG. 19 shows the transmission topology for two distal end-effector links, during an "force-applying" configuration, according to an embodiment of the current invention.

FIG. 18 shows the configuration where θ38=0. In this case, θ31=θ32=0, the end-effector remains closed while no gripping force is being applied between the end-effector links 31 and 32. To increase the gripping force of the end-effector 3, the replacement handle link 38 needs to be further moved towards the closing direction, by an angle θ38 (FIG. 19). This movement stretches the segments 36a and 37b and therefore increases the force of the end-effector link 31 against the end-effector link 32. This stretching of the cables (and consequent increase in gripping force) is higher than in the configuration shown in FIG. 13, due to the amplification factor α and by the fact that the two handle links 25, 26 are not physical colliding between them.

Figure 20:
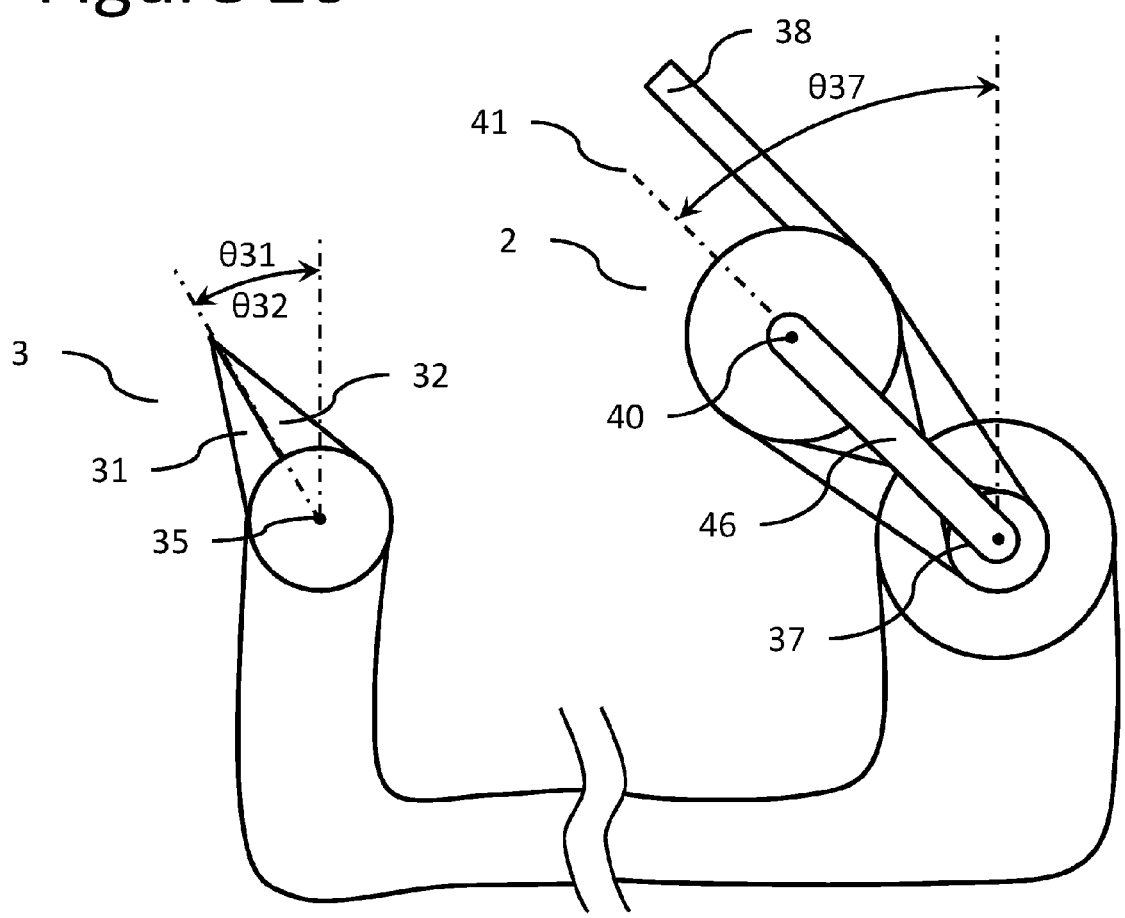
FIG. 20 shows the transmission topology for two distal end-effector links, during an "laterally oriented" configuration, according to an embodiment of the current invention.
Figure 21:
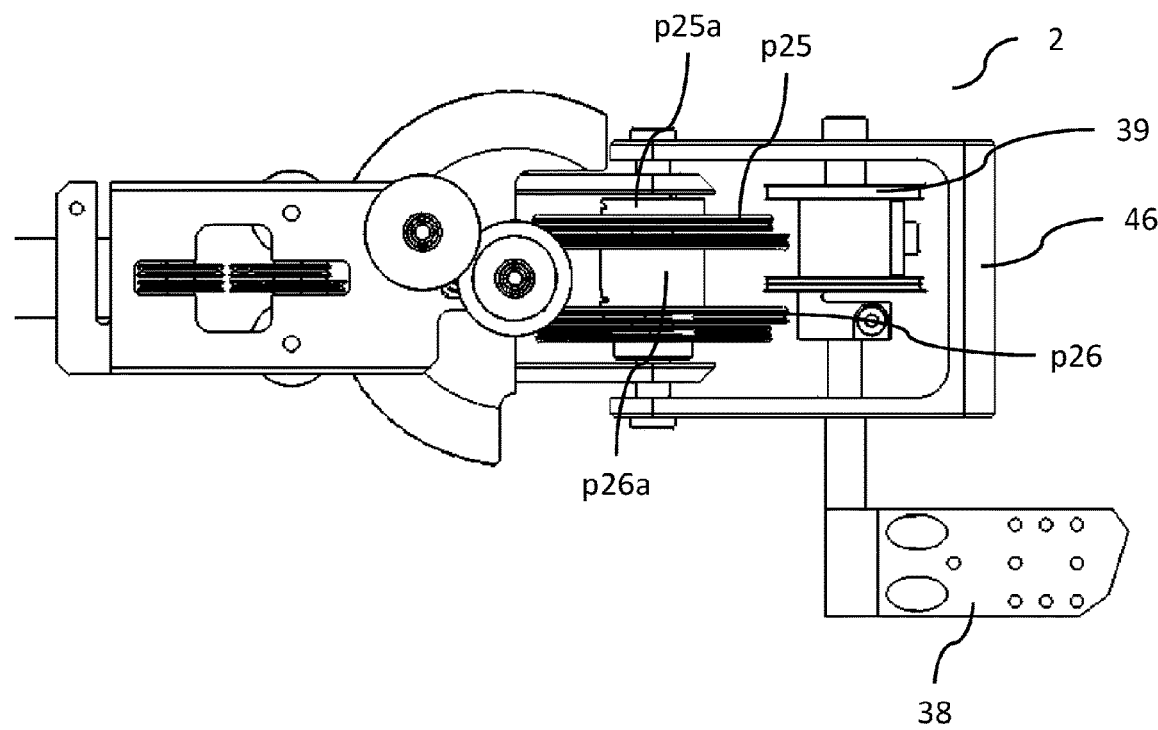
FIG. 21 shows a first perspective view of an articulated handle, according to an embodiment of the current invention.
Figure 22:
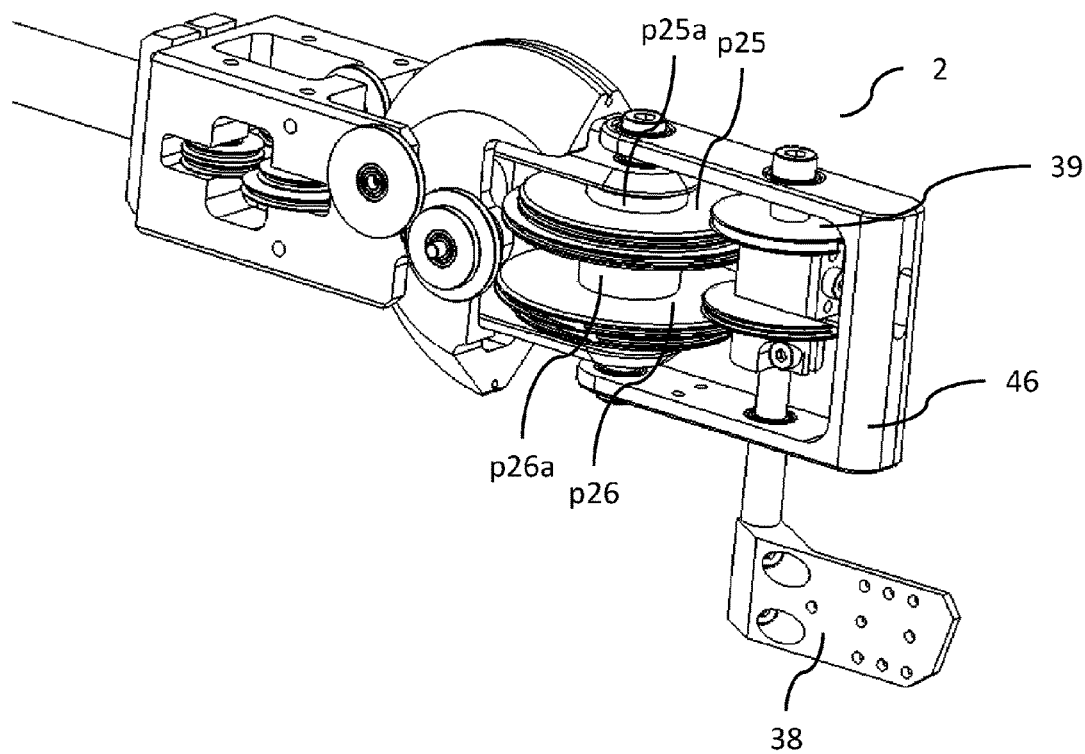
FIG. 22 shows a second perspective view of an articulated handle, according to an embodiment of the current invention.
Figure 23:
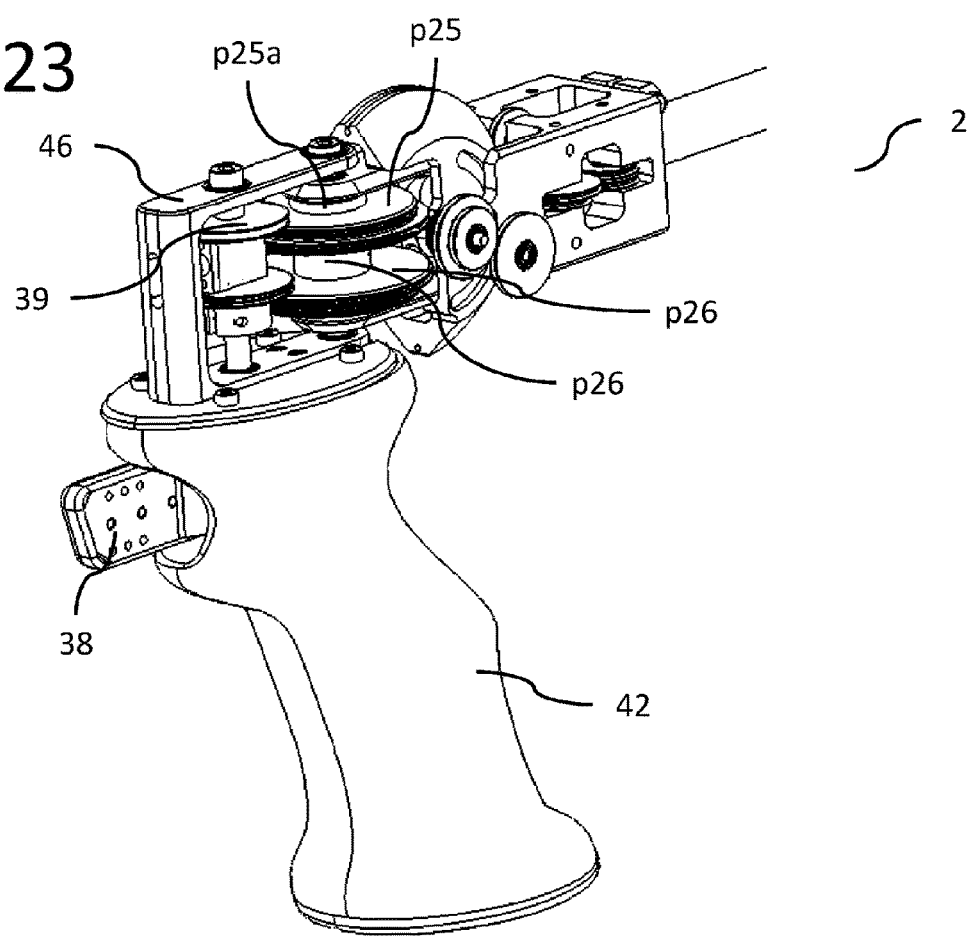
FIG. 23 shows a third perspective view of an articulated handle, according to an embodiment of the current invention.
Figure 24:
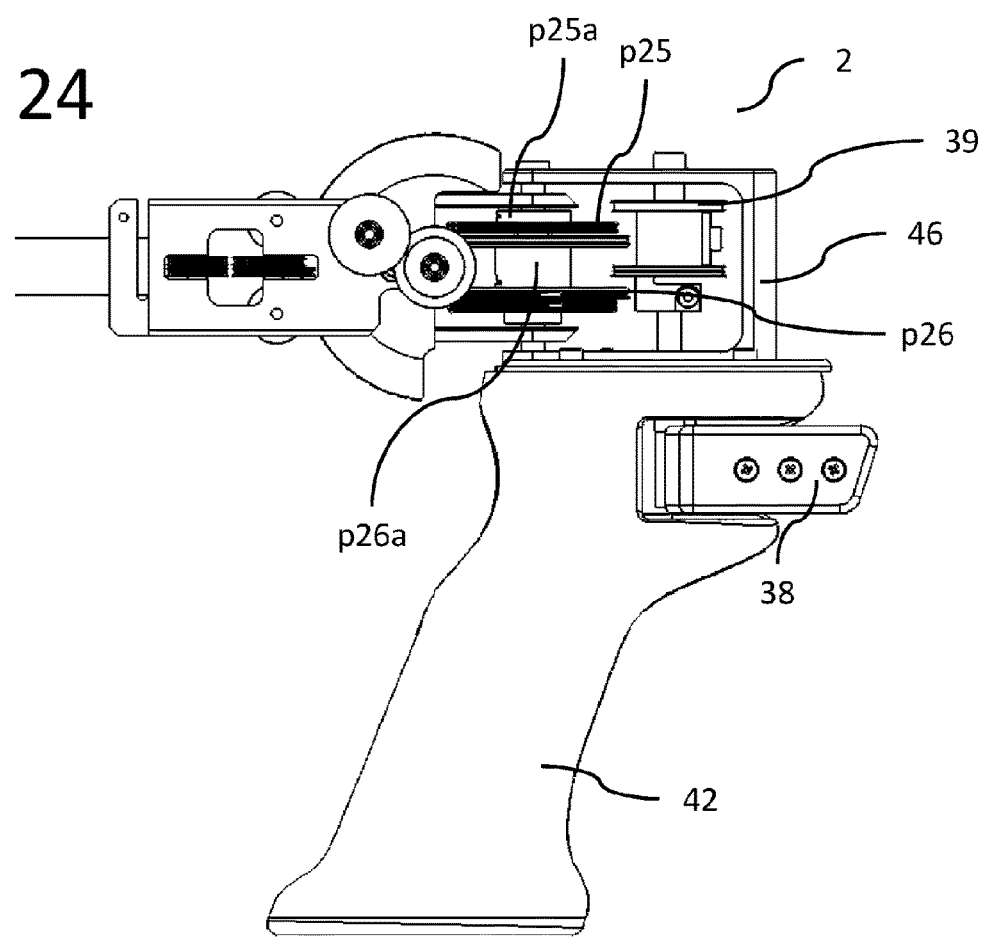
FIG. 24 shows a fourth perspective view of an articulated handle, according to an embodiment of the current invention.
Figure 25:
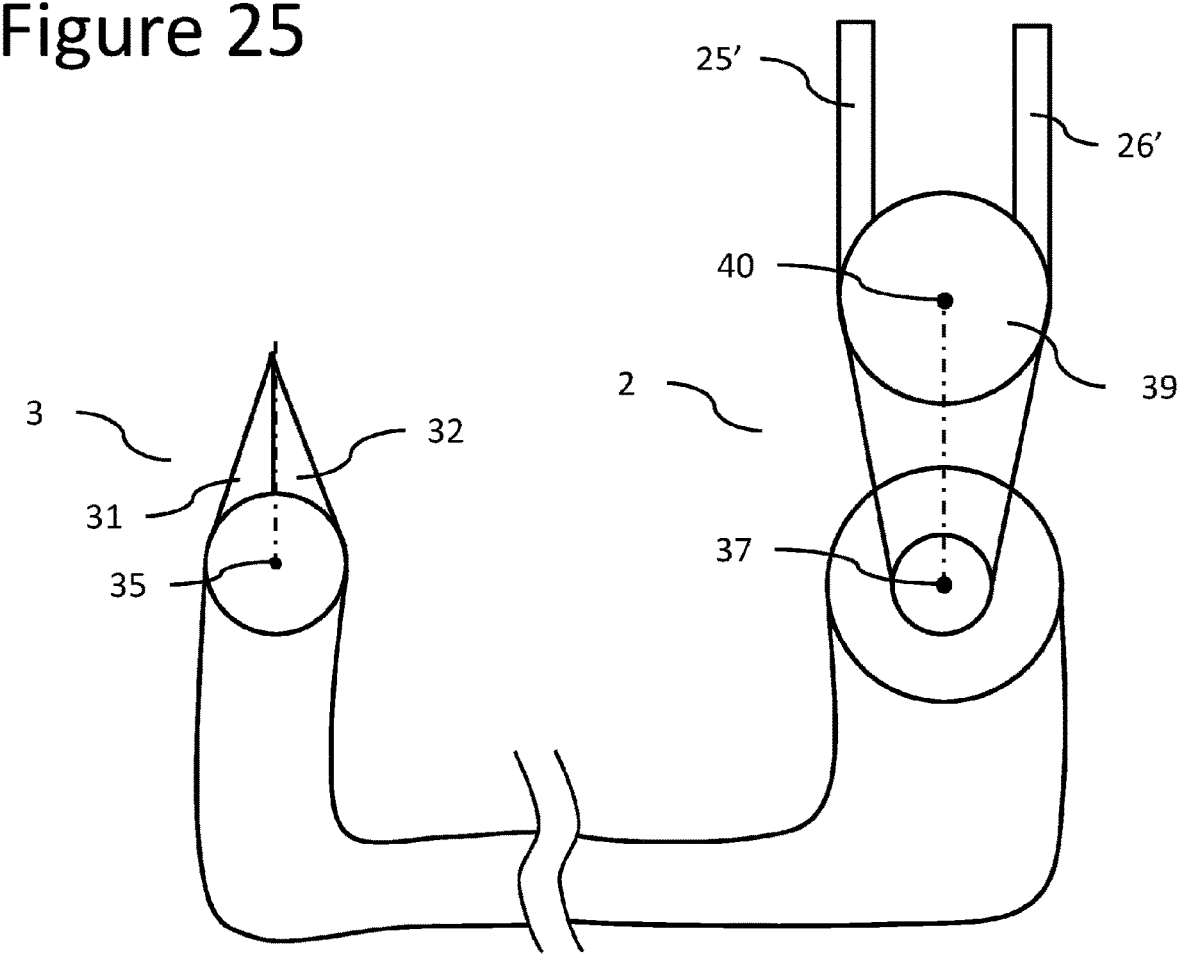
FIG. 25 shows the transmission topology for two distal end-effector links, during an "closed" configuration, according to an embodiment of the current invention.

In order to provide orientation motions θ31, θ32 between the end effector 3 and the slave link 29 (FIG. 8), the structural element 46 is rotated by and angle θ37, while the replacement handle link 38 remains stationary in relation to the structural element 46 (FIG. 20). This structural element 46 is able to pivot around the handle axis 37 and is where the second amplification pulleys p25b, p26b are mounted to rotate around the axis 40. This causes the end-effector link 31 and the end-effector link 32 to move θ31, θ32 in the same angle as θ37, with no amplification (θ31=θ33=θ37). However, a second amplification factor α2 could be used for these degrees of freedom.

FIGS. 21 to 24 show an embodiment of the handle 2 in different perspective views. A holder 42 may be attached to the handle 2 so that it can be more easily and ergonomically manipulated by the user.

Figure 26:
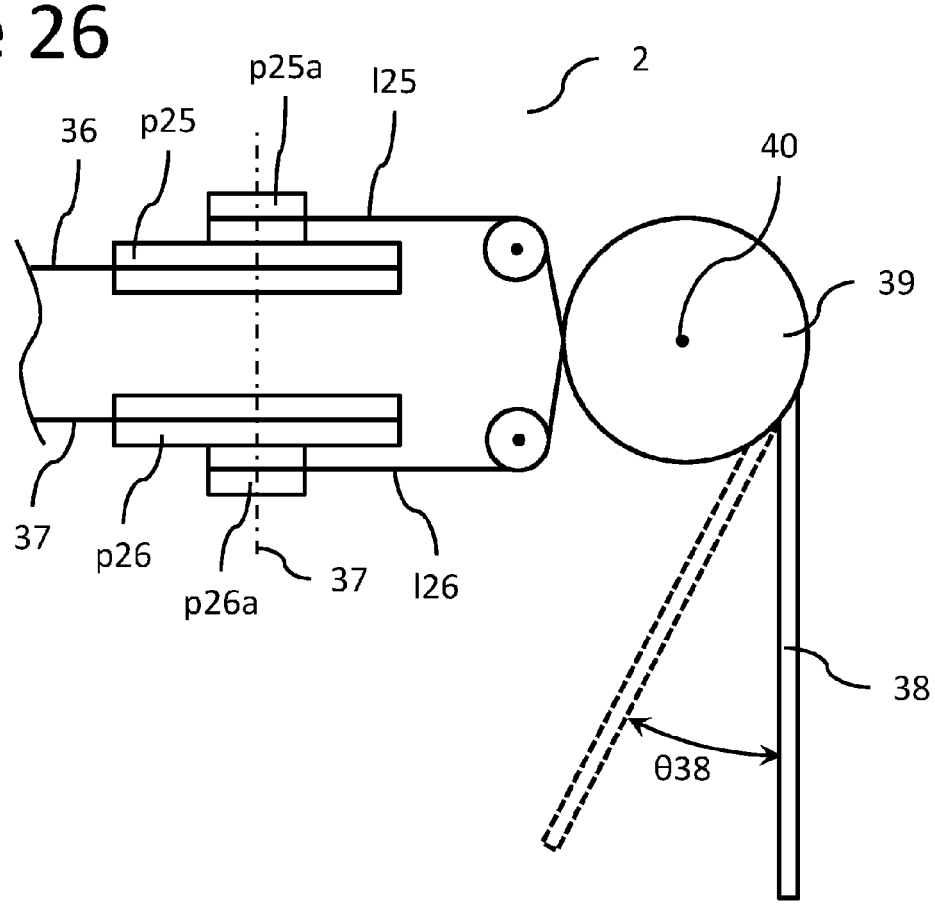
FIG. 26 shows a schematic side view of an articulated handle, according to an embodiment of the current invention.
Figure 27:
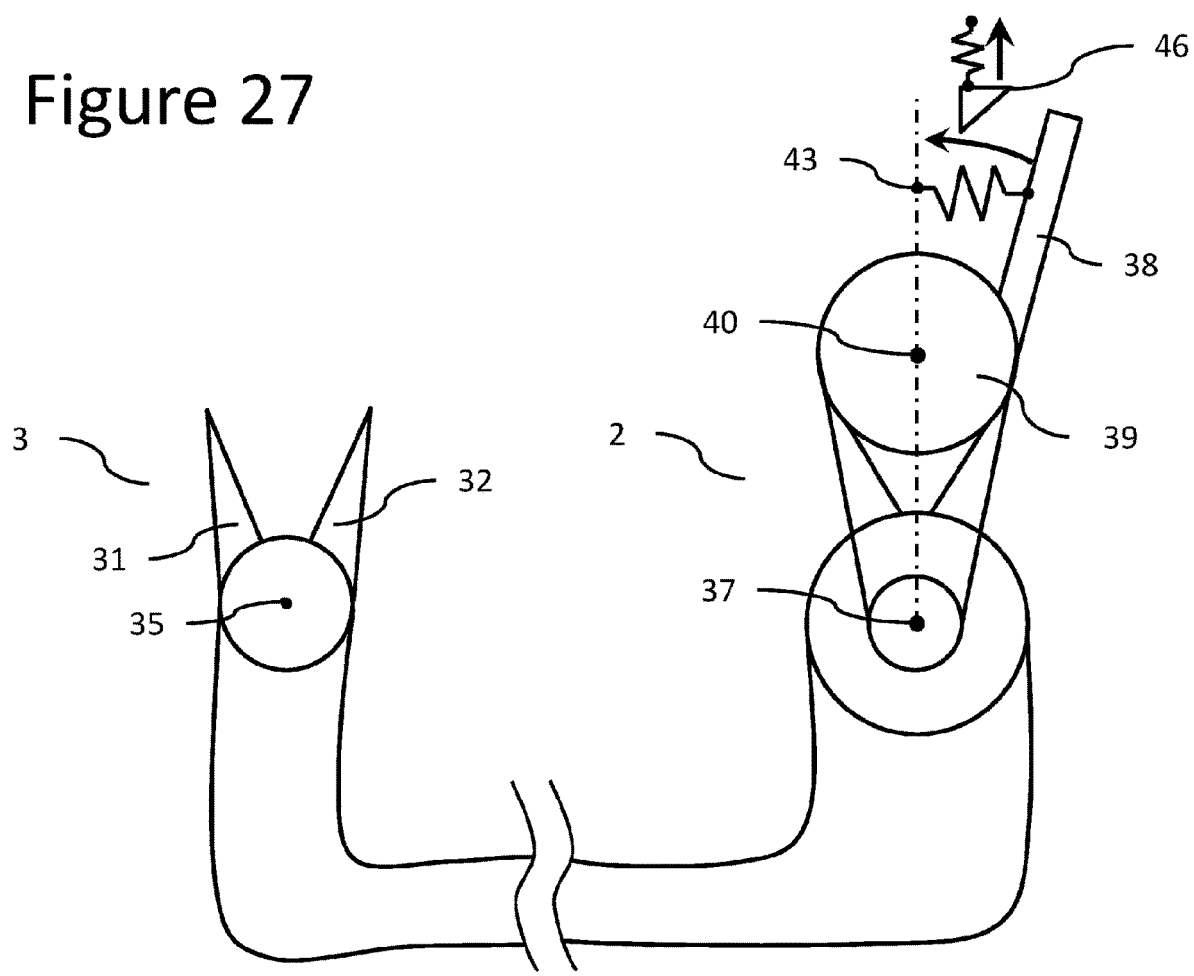
FIG. 27 shows the transmission topology for two distal end-effector links, during an "opened" configuration, according to an embodiment of the current invention.
Figure 32:
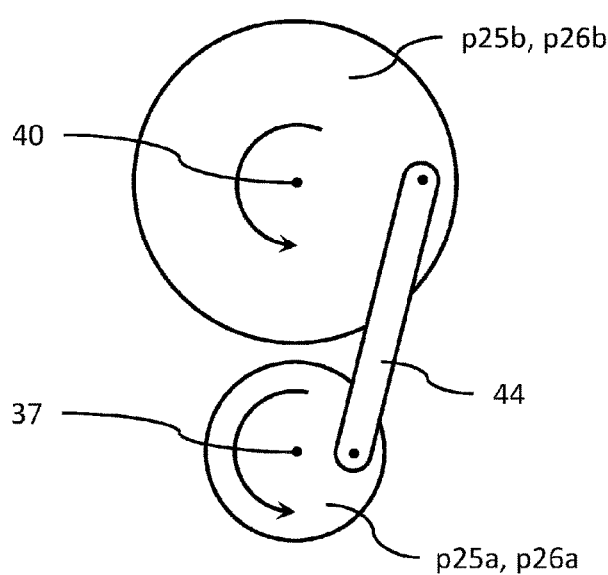
Figure 33:
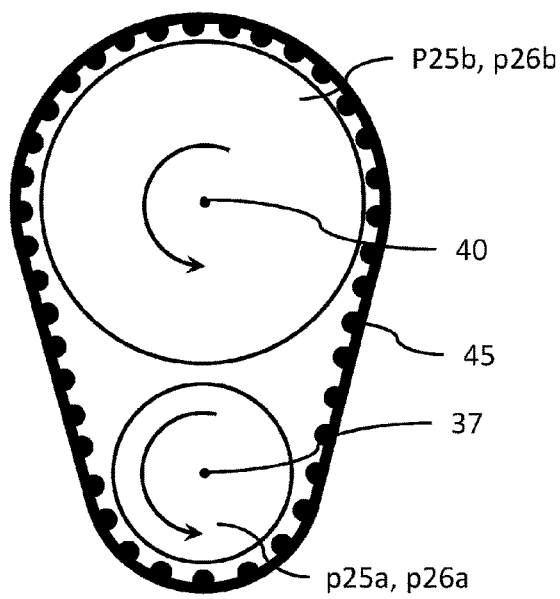

While this invention has been shown and described with reference to particular embodiments thereof, it will be understood by those skilled in the art that various changes in form and details may be made therein without departing from the spirit and scope of the invention as defined by the appended claims. For instance, the replacement handle link 25' and replacement handle link 26' may not be merged (FIG. 25) and the second axis 40, around which the second amplification pulley p26b is able to rotate, may be perpendicular and non-intersecting with the axis 37 (FIG. 26). In another embodiment, there can be a spring element 43 that can bring the replacement handle link 38 to an opened default position (FIG. 27).

Figure 34:
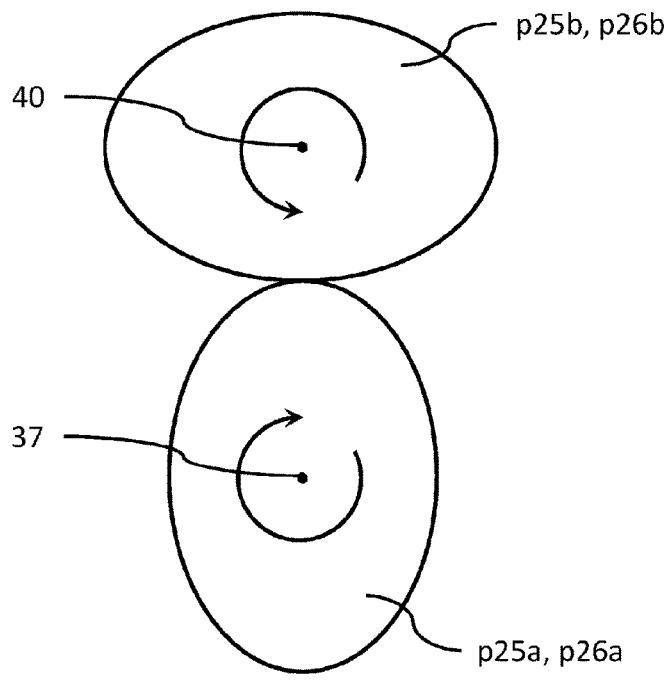
Figure 35:
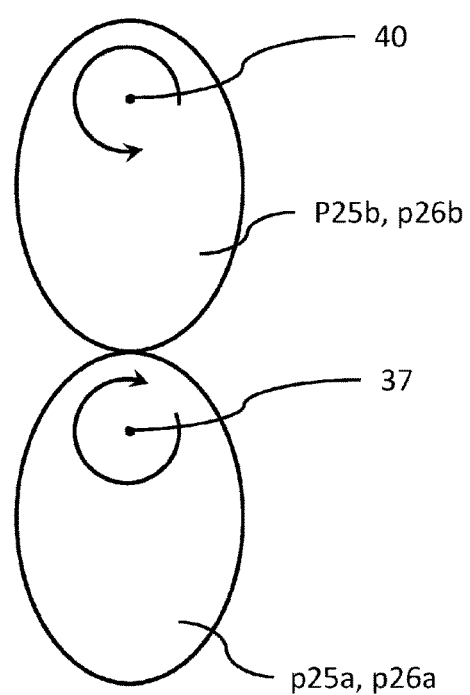

In other embodiments, the rotation can transmitted from first amplification pulleys p25a, p26a to the second amplification pulleys p25b, p26b by different mechanical solutions (FIGS. 28 to 33). In the previously described embodiments (FIGS. 14 to 27) the motion transmission is made by flexible elements 125a, 125b, 126a, 126b whose extremities are fixed to the first and second amplification pulleys p25a, p26a, p25b, p26b in a crossed (FIG. 28) and uncrossed (FIG. 29) configuration. In the embodiment of FIG. 30, the motion transmission is made by the friction force between the first amplification pulley p25a, p26a and second amplification pulley p25b, p26b. In the embodiment of FIG. 31, the motion transmission is made by a contact force (using teeth or other method to increase contact forces). In the embodiment of FIG. 34, the motion transmission is made by a push-pull element 44, which is pivotally connected to the first amplification pulley p25a, p26a and second amplification pulley p25b, p26b. In the embodiment of FIG. 35, the motion transmission is made by constant-pitch element 45 (which can take the form of a timing belt, a chain or a bead chain) that can engage the first amplification pulley p25a, p26a and second amplification pulley p25b, p26b. In still further embodiments, the embodiments previously described (FIGS. 28 to 33) can be used to transmit motion between non-circular first and second amplification pulleys p25a, p26a, p25b, p26b (FIG. 34) or to transmit motion between eccentrically rotating first and second amplification pulleys p25a, p26a, p25b, p26b (FIG. 35). In both the embodiments of FIGS. 32 and 33, non-constant amplification factors can be achieved.

Figure 36:
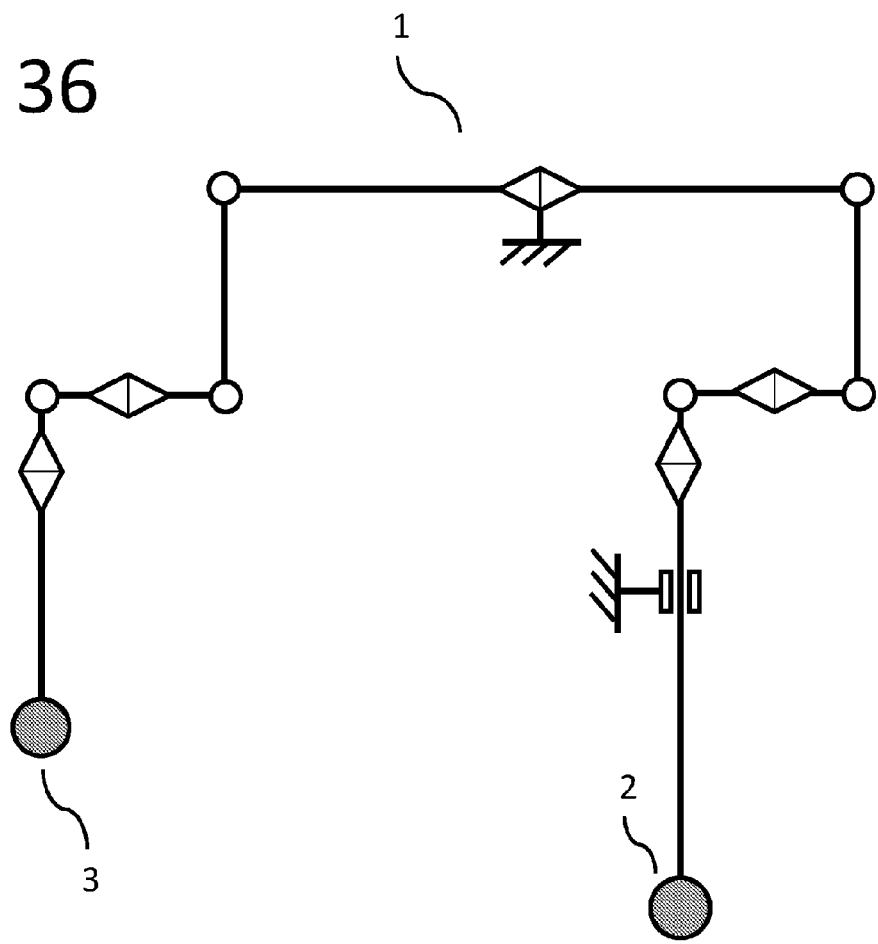
FIGS. 36 and 37 show a schematic view of a different mechanical telemanipulator kinematics where embodiments of the current invention can be applied.
Figure 37:
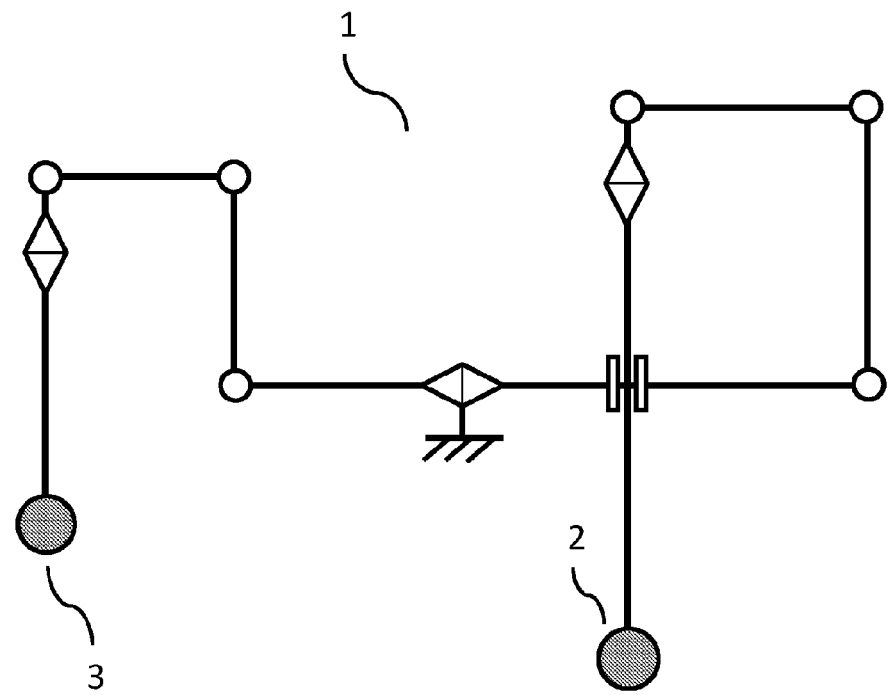
Figure 38:
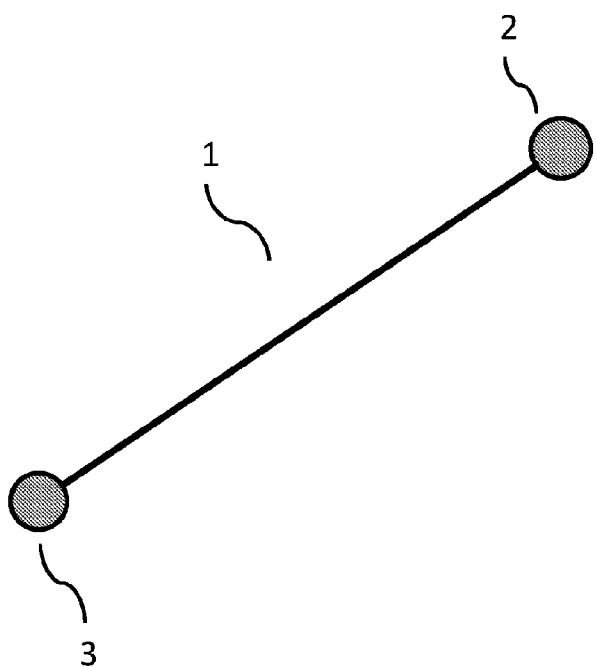
FIG. 38 shows the kinematics of a mechanical telemanipulator found in a hand-held embodiment of the present invention.

In other embodiments, the mechanical telemanipulator 1 can assume other kinematics, like the ones shown in FIGS. 36, 37 and 38 (hand-held device).

Figure 39:
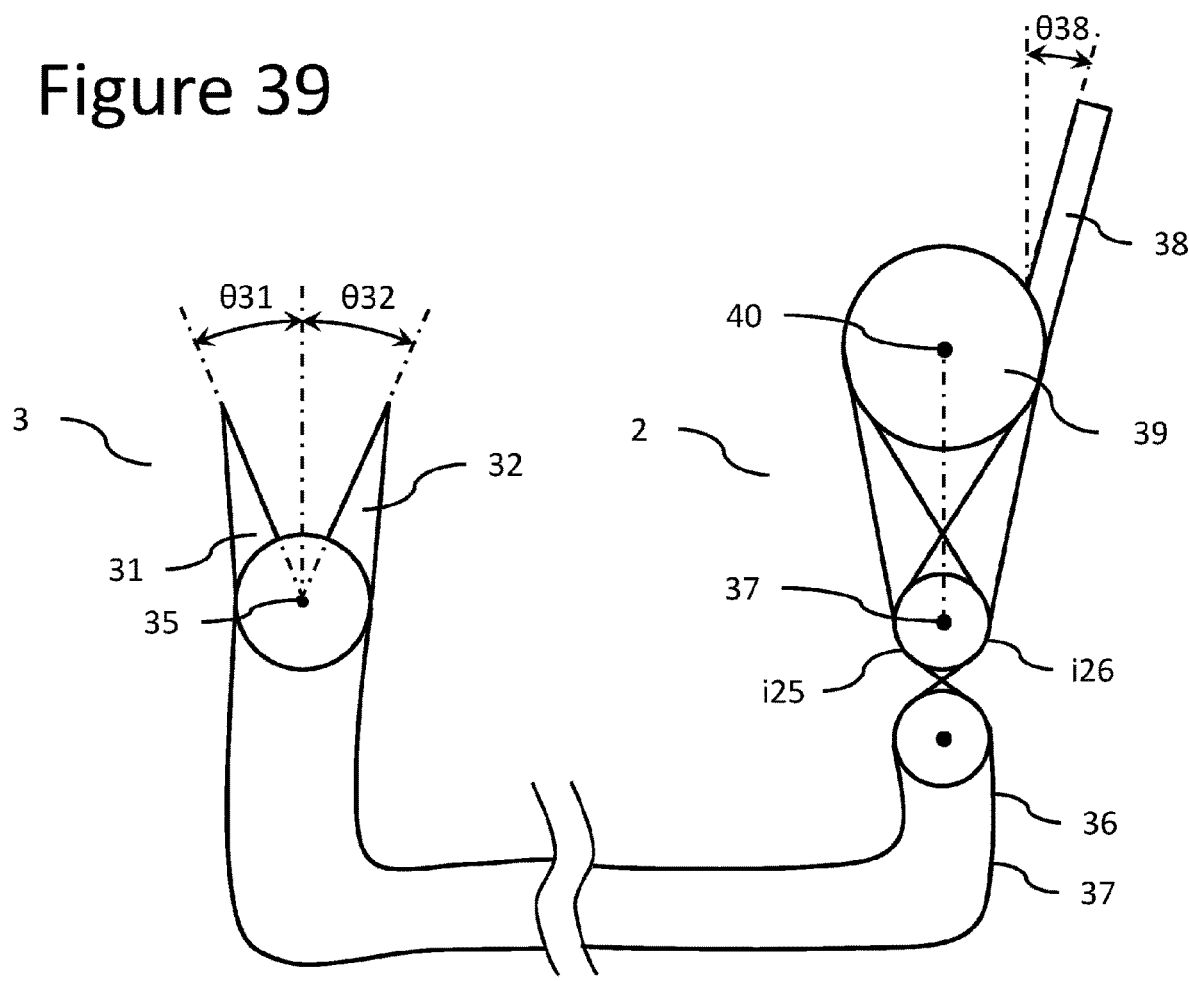
FIG. 39 displays the kinematics of a single cable loop embodiment of the present invention.

In another embodiment of the current invention, instead of having multiple cable loops to actuate each degree-of-freedom, single cable loops 37 and 36 are directly connecting the driven pulleys p32 and p31 to the amplification pulley 39 (FIG. 39). In this solution, the driving pulleys p26 and p25 are converted into idle pulleys i26 and i25 that are able to turn around the axis 37. In addition, the ratio between the diameters of the idle pulleys i26, i25 and the amplification pulley 39 correspond to the amplification factor α of the handle 2, which corresponds also to the ratio between the angles θ32 and θ31 of the end-effector link 32 and the angle θ38 of the replacement handle link 38 (θ32/θ38=α; θ31/θ38=α; Øi26/Ø39=α; Øi25/Ø39=α).

The invention claimed is:

1. An articulated handle for a mechanical telemanipulator comprising:
a plurality of handle links interconnected by a corresponding plurality of handle joints, at least one of the plurality of handle links coupled to a master link of a plurality of master links of a master manipulator, the plurality of master links interconnected by a corresponding plurality of master joints,
wherein the articulated handle is operatively coupled to an articulated end-effector comprising a plurality of end-effector links interconnected by a corresponding plurality of end-effector joints, at least one of the end-effector links coupled to a slave link of a plurality of slave links of a slave manipulator via a driven pulley, the plurality of slave links interconnected by a corresponding plurality of slave joints, such that movement applied to each master joint of the master manipulator is reproduced by the corresponding slave joint of the slave manipulator, and
wherein movement applied to a first handle link is reproduced, at a predetermined amplification, at a corresponding first end-effector link via an amplification pulley operatively coupled to the driven pulley.

2. The articulated handle of claim 1, wherein movement applied to a second handle link is reproduced, at a second predetermined amplification, at a corresponding second end-effector link.

3. The articulated handle of claim 1, wherein the angular movement of a single handle link is able to be reproduced, with a predetermined amplification factor, by two different end-effector links, which rotate in opposite directions.

4. The articulated handle of claim 1, wherein movement transmission between a handle link and an end-effector link is accomplished by a single loop flexible transmission element, comprising a flexible element selected from the group consisting of wires, chains, ropes and belts.

5. The articulated handle of claim 1, wherein movement transmission between a handle link and an end-effector link is accomplished by a multi loop transmission element.

6. The articulated handle of claim 5, wherein a proximal stage of the multi loop transmission element comprises a rigid linkage mechanism.

7. The articulated handle of claim 5, wherein a proximal stage of the multi loop transmission element is accomplished by contact force between at least two mechanical elements.

8. The articulated handle of claim 7, wherein the contact force between the at least two mechanical elements is maximized by the use of teethed geometries.

9. The articulated handle of claim 1, wherein the predetermined amplification is consistent with the movement applied to the first handle link.

10. The articulated handle of claim 1, wherein the predetermined amplification is inconsistent with the movement applied to the first handle link.

11. The articulated handle of claim 1, further comprising a spring element configured to bring the at least one handle link to a default position when it is not being actuated by a user and to bring the at least one end-effector link to a corresponding default position when the at least one handle link is not being actuated by the user.

12. The articulated handle of claim 1, wherein the mechanical telemanipulator has a hand-held configuration, without any base support, so that a user can control movement of the articulated end-effector only by actuating the articulated handle.

* * * * *